US008999679B2

(12) United States Patent
Che et al.

(10) Patent No.: US 8,999,679 B2
(45) Date of Patent: Apr. 7, 2015

(54) METHOD FOR ASSEMBLY OF POLYNUCLEIC ACID SEQUENCES

(75) Inventors: Austin Che, Boston, MA (US); Tom Knight, Boston, MA (US); Barry Canton, Boston, MA (US); Jason Kelly, Boston, MA (US); Reshma Shetty, Boston, MA (US)

(73) Assignee: Iti Scotland Limited, Glasgow (GB)

( * ) Notice: Subject to any disclaimer, the term of this patent is extended or adjusted under 35 U.S.C. 154(b) by 769 days.

(21) Appl. No.: 13/140,473

(22) PCT Filed: Dec. 18, 2009

(86) PCT No.: PCT/GB2009/002917

§ 371 (c)(1), (2), (4) Date: Sep. 8, 2011

(87) PCT Pub. No.: WO2010/070295

PCT Pub. Date: Jun. 24, 2010

(65) Prior Publication Data

US 2012/0040870 A1 Feb. 16, 2012

Related U.S. Application Data

(60) Provisional application No. 61/203,200, filed on Dec. 18, 2008.

(51) Int. Cl.

*C12N 15/66* (2006.01)
*C12N 15/10* (2006.01)
*C12N 15/64* (2006.01)

(52) U.S. Cl.

CPC ............ *C12N 15/66* (2013.01); *C12N 15/1093* (2013.01); *C12N 15/64* (2013.01)

(58) Field of Classification Search

None

See application file for complete search history.

(56) References Cited

U.S. PATENT DOCUMENTS

| | | | | |
|---|---|---|---|---|
| 5,258,292 | A * | 11/1993 | Yeh et al. | 435/128 |
| 5,362,489 | A * | 11/1994 | Kishimoto et al. | 424/85.2 |
| 6,521,427 | B1 | 2/2003 | Evans | |
| 2002/0025561 | A1 | 2/2002 | Hodgson | |
| 2002/0106680 | A1 | 8/2002 | Shinmyo et al. | |
| 2006/0281113 | A1 | 12/2006 | Church et al. | |
| 2007/0269870 | A1 | 11/2007 | Church et al. | |
| 2009/0087840 | A1 | 4/2009 | Baynes et al. | |

FOREIGN PATENT DOCUMENTS

| | | | |
|---|---|---|---|
| WO | 91/02077 | A1 | 2/1991 |
| WO | 99/14318 | A1 | 3/1999 |
| WO | 99/47536 | A2 | 9/1999 |
| WO | 00/49142 | A1 | 8/2000 |
| WO | 00/77181 | A2 | 12/2000 |
| WO | 01/88173 | A2 | 11/2001 |
| WO | 01/94366 | A1 | 12/2001 |
| WO | 03/044193 | A2 | 3/2003 |
| WO | 03/054232 | A2 | 7/2003 |
| WO | 03/085094 | A2 | 10/2003 |
| WO | 2004/035781 | A1 | 4/2004 |

(Continued)

OTHER PUBLICATIONS

Knight, Idempotent Vector Design for Standard Assembly of Biobricks (2003) MIT Articial Intelligence Laboratory, 11 pages.*

Gibson, D. G., et al., Enzymatic assembly of DNA molecules up to several hundred kilobases, Nat Methods. May 2009;6(5):343-5.

Ellis, T., et al., Diversity-based, model-guided construction of synthetic gene networks with predicted functions, Nat Biotechnol. May 2009;27(5):465-71.

Zeevi, V., et al., Increasing cloning possibilities using artificial zinc finger nucleases, Proc Natl Acad Sci U S A. Sep. 2, 2008;105(35):12785-90.

Lu, C., et al., Comparison of multiple gene assembly methods for metabolic engineering, Appl Biochem Biotechnol. Apr. 2007;137-140(1-12):703-10.

(Continued)

*Primary Examiner* — Jim Ketter

(74) *Attorney, Agent, or Firm* — Pepper Hamilton LLP

(57) ABSTRACT

The present invention provides a method for the assembly of a polynucleic acid sequence from a plurality of nucleic acid sequences in which the polynucleic acid sequence is of a formula $N_{n+1}$, in which N represents a nucleic acid sequence and where n is 1 or greater than 1 and each N may be the same or a different nucleic acid sequence, in which the method comprises: (i) providing a first nucleic acid sequence N1 which has an oligonucleotide linker sequence $L1^{3}$ at the 3'-end of the nucleic acid sequence; (ii) providing a second nucleic acid sequence N2 which optionally has an oligonucleotide linker sequence $L2^{3'}$ at the 3'-end of the nucleic acid sequence and which has an oligonucleotide linker sequence $L2^{5'}$ at the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1; (iii) optionally providing one or more additional nucleic acid sequences N, wherein nucleic acid sequence N2 has an oligonucleotide linker sequence $L2^{3'}$ at the 3'-end of the nucleic acid sequence, and wherein said one or more additional nucleic acid sequences N comprises a terminal additional nucleic acid sequence NZ, and wherein each additional nucleic acid sequence N has an oligonucleotide linker sequence at its 3'-end, wherein said terminal additional nucleic acid sequence NZ optionally lacks an oligonucleotide linker sequence at its 3'-end and wherein each additional nucleic acid sequence N has an oligonucleotide linker sequence at its 5'-end, wherein for the first additional nucleic acid sequence N3 the 5'-end linker sequence $L3^{5'}$ is complementary to the 3'-end linker sequence $L2^{3'}$ of nucleic acid sequence N2 and for each second and subsequent additional nucleic acid sequence N the 5'-end linker sequence is complementary to the 3'-end linker sequence of the respective preceding additional nucleic acid sequence; and (iv) ligating said nucleic acid sequences to form said polynucleic acid sequence.

16 Claims, 24 Drawing Sheets

(56) References Cited

FOREIGN PATENT DOCUMENTS

| | | | |
|---|---|---|---|
| WO | 2005/051970 | A2 | 6/2005 |
| WO | 2005/071077 | A1 | 8/2005 |
| WO | 2005/071111 | A1 | 8/2005 |
| WO | 2006/044956 | A1 | 4/2006 |
| WO | 2006/127423 | A2 | 11/2006 |
| WO | 2007/032859 | A2 | 3/2007 |
| WO | 2007/040592 | A1 | 4/2007 |
| WO | 2007/123742 | A2 | 11/2007 |
| WO | 2007/136736 | A2 | 11/2007 |
| WO | 2007/136834 | A2 | 11/2007 |
| WO | 2007/137242 | A2 | 11/2007 |
| WO | 2008/024129 | A2 | 2/2008 |
| WO | 2008/024176 | A2 | 2/2008 |
| WO | 2008/027558 | A2 | 3/2008 |
| WO | WO2008075368 | A1 | 6/2008 |
| WO | 2008/127283 | A2 | 10/2008 |
| WO | 2008/144192 | A1 | 11/2008 |
| WO | 2009/020435 | A1 | 2/2009 |
| WO | 2009/149218 | A2 | 12/2009 |
| WO | 2010/025310 | A2 | 3/2010 |

OTHER PUBLICATIONS

Tsuge, K., et al., One step assembly of multiple DNA fragments with a designed order and orientation in *Bacillus subtilis* plasmid, Nucleic Acids Res. Nov. 1, 2003;31(21):e133.

Zhou, X., et al., Microfluidic PicoArray synthesis of oligodeoxynucleotides and simultaneous assembling of multiple DNA sequences, Nucleic Acids Res. Oct. 11, 2004;32(18):5409-17.

Xiong, A. S., et al., Non-polymerase-cycling-assembly-based chemical gene synthesis: strategies, methods, and progress, Biotechnol Adv. Mar.-Apr. 2008;26(2):121-34.

Kong, D. S., et al., Parallel gene synthesis in a microfluidic device, Nucleic Acids Res. 2007;35(8):e61.

Lewin, Genes IV, Oxford University Press; 4th edition, 1990, pp. 453-456.

Sambrook, Molecular Cloning, A Laboratory Manual, Cold Spring Harbor Laboratory Press; 3rd edition, 2001, pp. 8.22-8.26.

* cited by examiner

```
pSB1C3.GFP.kanR
        misc_feature    1..103
                        /note="pSB1C3"

        misc_feature    104..106
                        /note="S_L overhang"

        primer_bind     107..151
                        /note="Part/Linker Oligos"

        misc_feature    152..154
                        /note="S_P overhang"

        misc_feature    155..1119
                        /note="I7101 (GFP)"

        misc_feature    1120..1122
                        /note="S_L overhang"

        primer_bind     1123..1167
                        /note="Part/Linker Oligos"

        misc_feature    1168..1170
                        /note="S_P overhang"

        misc_feature    1171..2164
                        /note="P1003 (kanR)"

        misc_feature    2165..2167
                        /note="S_L overhang"

        primer_bind     2168..2212
                        /note="Part/Linker Oligos"

        misc_feature    2213..2215
                        /note="S_P overhang"

        misc_feature    2216..>4168
                        /note="pSB1C3"
ORIGIN
        1 cattaaccta taaaaatagg cgtatcacga ggcagaattt cagataaaaa aaatccttag
       61 ctttcgctaa ggatgatttc tggaattcgc ggccgcttct agagccacac gcgctctccc
      121 ccagtgtgag agtgtggggg agagcgcgtg tccgtctaga gtccctatca gtgatagaga
      181 ttgacatccc tatcagtgat agagatactg agcactacta gagtcacaca ggaaagtact
      241 agatgcgtaa aggagaagaa cttttcactg gagttgtccc aattcttgtt gaattagatg
      301 gtgatgttaa tgggcacaaa ttttctgtca gtggagaggg tgaaggtgat gcaacatacg
      361 gaaaacttac ccttaaattt atttgcacta ctggaaaact acctgttcca tggccaacac
      421 ttgtcactac tttcggttat ggtgttcaat gctttgcgag atacccagat catatgaaac
      481 agcatgactt tttcaagagt gccatgcccg aaggttatgt acaggaaaga actatatttt
      541 tcaaagatga cgggaactac aagacacgtg ctgaagtcaa gtttgaaggt gatacccttg
      601 ttaatagaat cgagttaaaa ggtattgatt ttaaagaaga tggaaacatt cttggacaca
      661 aattggaata caactataac tcacacaatg tatacatcat ggcagacaaa caaaagaatg
      721 gaatcaaagt taacttcaaa attagacaca acattgaaga tggaagcgtt caactagcag
      781 accattatca acaaaatact ccaattggcg atggccctgt ccttttacca gacaaccatt
      841 acctgtccac acaatctgcc ctttcgaaag atcccaacga aaagagagac cacatggtcc
      901 ttcttgagtt tgtaacagct gctgggatta cacatggcat ggatgaacta tacaaataat
      961 aatactagag ccaggcatca aataaaacga aaggctcagt cgaaagactg ggcctttcgt
     1021 tttatctgtt gtttgtcggt gaacgctctc tactagagtc acactggctc accttcgggt
     1081 gggcctttct gcgtttatat actagtagcg gccgctgcag ccacacgcgc tctcccccat
     1141 cctaccatcc tgggggagag cgcgtgtccg tctagagctg atccttcaac tcagcaaaag
     1201 ttcgatttat tcaacaaagc cacgttgtgt ctcaaaatct ctgatgttac attgcacaag
     1261 ataaaaatat atcatcatga acaataaaac tgtctgctta cataaacagt aatacaaggg
     1321 gtgttatgag ccatattcaa cgggaaacgt cttgctcccg tccgcgctta aactccaaca
     1381 tggacgctga tttatatggg tataaatggg ctcgcgataa tgtcgggcaa tcaggtgcga
     1441 caatctatcg cttgtatggg aagcccgatg cgccagagtt gtttctgaaa catggcaaag
     1501 gtagcgttgc caatgatgtt acagatgaga tggtccgtct caactggctg acggagttta
```

FIG. 21

```
1561 tgcctctccc gaccatcaag cattttatcc gtactcctga tgatgcgtgg ttactcacca
1621 ccgcgattcc tgggaaaaca gccttccagg tattagaaga atatcctgat tcaggtgaaa
1681 atattgttga tgcgctggcc gtgttcctgc gccggttaca ttcgattcct gtttgtaatt
1741 gtccttttaa cagcgatcgt gtatttcgtc ttgctcaggc gcaatcacgc atgaataacg
1801 gtttggttga tgcgagtgat tttgatgacg agcgtaatgg ctggcctgtt gaacaagtct
1861 ggaaagaaat gcacaagctc ttgccattct caccggattc agtcgtcact catggtgatt
1921 tctcacttga taaccttatt tttgacgagg ggaaattaat aggttgtatt gatgttggac
1981 gggtcggaat cgcagaccgt taccaggacc ttgccattct ttggaactgc ctcggtgagt
2041 tttctccttc attacagaaa cggctttttc aaaaatatgg tattgataat cctgatatga
2101 ataaattgca gtttcatttg atgctcgatg agtttttcta atcatactag tagcggccgc
2161 tgcagccaca cgcgctctcc cccaccaacc ccaattgggg gagagcgcgt gtccgctgca
2221 gtccggcaaa aaaacgggca aggtgtcacc accctgccct ttttctttaa aaccgaaaag
2281 attacttcgc gttatgcagg cttcctcgct cactgactcg ctgcgctcgg tcgttcggct
2341 gcggcgagcg gtatcagctc actcaaaggc ggtaatacgg ttatccacag aatcagggga
2401 taacgcagga aagaacatgt gagcaaaagg ccagcaaaag gccaggaacc gtaaaaaggc
2461 cgcgttgctg gcgtttttcc ataggctccg cccccctgac gagcatcaca aaaatcgacg
2521 ctcaagtcag aggtggcgaa acccgacagg actataaaga taccaggcgt ttccccctgg
2581 aagctccctc gtgcgctctc ctgttccgac cctgccgctt accggatacc tgtccgcctt
2641 tctcccttcg ggaagcgtgg cgctttctca tagctcacgc tgtaggtatc tcagttcggt
2701 gtaggtcgtt cgctccaagc tgggctgtgt gcacgaaccc cccgttcagc ccgaccgctg
2761 cgccttatcc ggtaactatc gtcttgagtc caacccggta agacacgact tatcgccact
2821 ggcagcagcc actggtaaca ggattagcag agcgaggtat gtaggcggtg ctacagagtt
2881 cttgaagtgg tggcctaact acggctacac tagaaggaca gtatttggta tctgcgctct
2941 gctgaagcca gttaccttcg gaaaaagagt tggtagctct tgatccggca aacaaaccac
3001 cgctggtagc ggtggttttt ttgtttgcaa gcagcagatt acgcgcagaa aaaaaggatc
3061 tcaagaagat cctttgatct tttctacggg gtctgacgct cagtggaacg aaaactcacg
3121 ttaagggatt ttggtcatga gattatcaaa aaggatcttc acctagatcc ttttaaatta
3181 aaaatgaagt tttaaatcaa tctaaagtat atatgagtaa acttggtctg acagctcgag
3241 gcttggattc tcaccaataa aaaacgcccg gcggcaaccg agcgttctga acaaatccag
3301 atggagttct gaggtcatta ctggatctat caacaggagt ccaagcgagc tcgatatcaa
3361 attacgcccc gccctgccac tcatcgcagt actgttgtaa ttcattaagc attctgccga
3421 catggaagcc atcacaaacg gcatgatgaa cctgaatcgc cagcggcatc agcaccttgt
3481 cgccttgcgt ataatatttg cccatggtga aaacgggggc gaagaagttg tccatattgg
3541 ccacgtttaa atcaaaactg gtgaaactca cccagggatt ggctgagacg aaaaacatat
3601 tctcaataaa ccctttaggg aaataggcca ggttttcacc gtaacacgcc acatcttgcg
3661 aatatatgtg tagaaactgc cggaaatcgt cgtggtattc actccagagc gatgaaaacg
3721 tttcagtttg ctcatggaaa acggtgtaac aagggtgaac actatcccat atcaccagct
3781 caccgtcttt cattgccata cgaaattccg gatgagcatt catcaggcgg gcaagaatgt
3841 gaataaaggc cggataaaac ttgtgcttat ttttctttac ggtctttaaa aaggccgtaa
3901 tatccagctg aacggtctgg ttataggtac attgagcaac tgactgaaat gcctcaaaat
3961 gttctttacg atgccattgg gatatatcaa cggtggtata tccagtgatt tttttctcca
4021 ttttagcttc cttagctcct gaaaatctcg ataactcaaa aaatacgccc ggtagtgatc
4081 ttatttcatt atggtgaaag ttggaacctc ttacgtgccc gatcaactcg agtgccactt
4141 gacgtctaag aaaccattat tatcatga
```

METHOD FOR ASSEMBLY OF POLYNUCLEIC ACID SEQUENCES

BACKGROUND TO THE INVENTION

Synthetic biology brings together the disciplines of engineering, biology and bioinformatics. Its focus is to make the engineering of biology easier and more predictable. The basis of synthetic biology is the production of genetic pathways using nucleic acid sequences as "building blocks". Technological applications of synthetic biology include the production of biofuels, environmentally friendly chemicals, drugs and new materials.

In order to meet the challenge of combinatorial assembly of many genetic pathways in parallel at a reasonable cost, it is necessary to re-think typical approaches for assembly of nucleic acids. For pathways containing a large number of genes and associated regulation and control elements, existing pairwise, hierarchical assembly approaches require a significant number of assembly stages that render the approaches impractical. For instance, a pathway with 30 components (e.g., 10 genes with associated regulation and control elements) would require 5 rounds of hierarchical assembly. In order to make hundreds or thousands of such pathways, the liquid handling alone needed between each round of assembly would render the approach impractical.

The BioBricks™ system (Cambridge, Mass.) allows for the assembly of up to 3 "parts" or nucleic acid sequences (typically genes and associated regulation and control elements) at once by making use of standardised parts and restriction enzymes.

Gibson et al (Nature Methods 6(5): 343-345, 2009) relates to a method for enzymatic assembly of DNA molecules of up to several hundred kilobases. The method is an isothermal, single-reaction method for assembling multiple overlapping DNA molecules by the concerted action of a 5' exonuclease, a DNA polymerase and a DNA ligase. The method therefore requires a number of different enzymes and requires the DNA molecules that are to be assembled to have a long stretch of overlapping sequence. In practice, this means that the DNA molecules need to be made de novo for each assembly.

Ellis et al (Nature Biotechnology 27(5): 465-471. 2009) relates to diversity-based, model guided construction of gene networks with predicted functions. The approach couples libraries of diversified components (synthesizes with randomized nonessential sequence) with in silico modelling.

There is therefore a need in the art for a method for combinatorial assembly of nucleic acid sequences such as genes and associated regulation and control elements that allows for the fast and reliable construction of large genetic pathways using minimal reagents.

SUMMARY OF THE INVENTION

The present inventors have devised a method for the combinatorial assembly of nucleic acid sequences which overcomes the disadvantages of the prior art. The method is a "one pot" method and is thus much quicker and more convenient to use than the hierarchical assembly approaches described in the prior art which require the nucleic acid sequences to be assembled in a pre-defined order. In addition, the method does not require the custom synthesis of nucleic acid sequences. The method makes use of oligonucleotide linkers that can be attached to any standardized nucleic acid sequence, allowing for the quick and simple assembly of polynucleic acid sequences from multiple shorter nucleic acid sequences.

According to a first aspect, the present invention provides a method for the assembly of a polynucleic acid sequence from a plurality of nucleic acid sequences in which the polynucleic acid sequence is of a formula $N_{n+1}$, in which N represents a nucleic acid sequence and where n is 1 or greater than 1 and each N may be the same or a different nucleic acid sequence, in which the method comprises:

(i) providing a first nucleic acid sequence N1 which has an oligonucleotide linker sequence $L1^{3'}$ at the 3'-end of the nucleic acid sequence;

(ii) providing a second nucleic acid sequence N2 which optionally has an oligonucleotide linker sequence $L2^{3'}$ at the 3'-end of the nucleic acid sequence and which has an oligonucleotide linker sequence $L2^{5'}$ at the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1;

(iii) optionally providing one or more additional nucleic acid sequences N, wherein nucleic acid sequence N2 has an oligonucleotide linker sequence $L2^{3'}$ at the 3'-end of the nucleic acid sequence, and wherein said one or more additional nucleic acid sequences N comprises a terminal additional nucleic acid sequence NZ, and wherein each additional nucleic acid sequence N has an oligonucleotide linker sequence at its 3'-end, wherein said terminal additional nucleic acid sequence NZ optionally lacks an oligonucleotide linker sequence at its 3'-end and wherein each additional nucleic acid sequence N has an oligonucleotide linker sequence at its 5'-end, wherein for the first additional nucleic acid sequence N3 the 5'-end linker sequence $L3^{5'}$ is complementary to the 3'-end linker sequence $L2^{3'}$ of nucleic acid sequence N2 and for each second and subsequent additional nucleic acid sequence N the 5'-end linker sequence is complementary to the 3'-end linker sequence of the respective preceding additional nucleic acid sequence; and (iv) ligating said nucleic acid sequences to form said polynucleic acid sequence.

Definitions

As used herein, the term "polynucleic acid sequence" means a polymer of nucleic acids.

As used herein, the term "nucleic acid" means a polymer of nucleotides. Nucleotides are sometimes referred to as bases (in single stranded nucleic acid molecules) or as base pairs (bp, in double stranded nucleic acid molecules). The term "nucleic acid" is used interchangeably herein with the term "part" and with the term "polynucleotide". A "nucleic acid" or "polynucleotide" as defined herein includes a plurality of oligonucleotides as defined herein.

Nucleic acids for use in the present invention are typically the naturally-occurring nucleic acids DNA or RNA, but can also be artificial nucleic acids such as PNA (peptide nucleic acid), LNA (locked nucleic acid), UNA (unlocked nucleic acid), GNA (glycol nucleic acid) and TNA (threose nucleic acid). Nucleic acids such as DNA for use in the invention can be synthetic or natural.

Nucleic acids for use in the present invention typically consist of the nucleotides adenine (A), cytosine (C), guanine (G), thymine (T) and uracil (U). Modified nucleotides that can also be used in the present invention include 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxylcarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine and 2-O-methyluridine.

The length of a nucleic acid sequence or polynucleotide can be measured in terms of the number of nucleotides it contains. The term "kilobase" (kb) means 1000 nucleotides.

As used herein, the term "oligonucleotide" means a polymer of nucleotides (i.e. at least 2 nucleotides) that is shorter in length than a "nucleic acid" as defined herein. The term "oligonucleotide" is sometimes abbreviated herein to "oligo". Typically, an oligonucleotide consists of up to 40 nucleotides or bases, more typically up to 60 nucleotides or bases. Typically, an oligonucleotide is sufficiently short that it has no secondary or tertiary structure.

As used herein, the terms "3'" ("3 prime") and "5'" ("5 prime") take their usual meanings in the art, i.e. to distinguish the ends of a nucleic acid molecules. As used herein, the terms 3' and 5' are also referred to using the nomenclature 5' and 3'. Nucleic molecules each have a 5' and a 3' end. Nucleic acids are synthesised in vivo in a 5' to 3' direction, and nucleic acid sequences are conventionally written in a 5' to 3' direction.

As used herein, the term "ligating" means joining together.

As used herein, the term "overhang" means a stretch of unpaired nucleotides at the end of a nucleic acid, polynucleotide or oligonucleotide.

As used herein, the term "synthetic genome" means a polynucleic acid sequence that contains the information for a functioning organism or organelle to survive and, optionally, replicate itself. The genome can be completely or partially constructed from components that have been chemically synthesized (e.g. synthetic DNA) or from copies of chemically synthesized nucleic acid components. The synthetic genome can be a completely synthetic genome, i.e. constructed entirely from nucleic acid that has been chemically synthesized, or from copies of chemically synthesized nucleic acid components. The synthetic genome can alternatively be a partially synthetic genome, i.e. constructed partially from nucleic acid that has been chemically synthesized and partially from naturally occurring nucleic acid. A partially synthetic genome as defined herein can include nucleic acid derived from any species of prokaryote or eukaryote, and/or elements from different species.

In all definitions, the singular and plural are used interchangeably.

DETAILED DESCRIPTION OF THE INVENTION

The present invention provides a method for the assembly of a polynucleic acid sequence from a plurality of nucleic acid sequences. The method of the invention thus involves the production of a long nucleic acid sequence from a number of shorter nucleic acid sequences.

In the method of the invention, the nucleic acid sequences are assembled such that the polynucleic acid includes a plurality of nucleic acid sequences in a predetermined order. For example, the method of the invention can be used to assemble a gene or series of genes together with their associated regulatory and control elements, thus producing a complete operon. The method of the invention is thus useful in the combinatorial assembly of genetic pathways, for example metabolic pathways and synthetic pathways. In one embodiment, the method of the invention is useful in the production of a synthetic genome.

In the method of the present invention, the polynucleic acid sequence is of a formula $N_{n+1}$, in which N represents a nucleic acid sequence and where n is 1 or greater than 1. The method of the present invention is therefore used to produce a polynucleic acid sequence containing 2 or more nucleic acid sequences. The polynucleic acid sequence produced by the method of the present invention is not limited to a polynucleic acid sequence having a particular number of nucleic acid sequences or parts. However, the polynucleic acid sequence typically contains from 2 to 20, typically from 3 to 15, from 4 to 10, from 5 to 9, from 6 to 8 nucleic acid sequences. Typically, the polynucleic acid sequence contains 2, 3, 4, 5, 6, 7, 8, 9 or 10 nucleic acid sequences. Thus, n is typically 2, 3, 4, 5, 6, 7, 8, 9 or 10 and the polynucleic acid sequence produced is typically of the formula $N_2$ to $N_{10}$, i.e. the polynucleic acid sequence produced is of the formula $N_2$, $N_S$, $N_4$, $N_5$, $N_6$, $N_7$, $N_8$, $N_9$ or $N_{10}$.

The polynucleic acid produced by the method of the present invention typically comprises at least 1000 nucleotides. Typically, the polynucleic acid produced by the method of the present invention comprises between 1000 and 50000 nucleotides, typically between 2000 and 40000 nucleotides, typically between 3000 and 30000 nucleotides, typically between 4000 and 25000 nucleotides, typically between 5000 and 20000 nucleotides, typically between 6000 and 15000 nucleotides, typically between 7000 and 13000 nucleotides, typically between 8000 and 12000 nucleotides, typically between 9000 and 11000 nucleotides, typically around 10000 nucleotides.

Typically, the polynucleic acid sequence is from 10 kb to 30 kb. However, the polynucleic acid can be from 10 kb to 30 kb, 40 kb, 50 kb, 75 kb, 100 kb, 120 kb, 140 kb or 150 kb. In some embodiments, the polynucleic acid is at least 150 kb, at least 200 kb, at least 250 kb, at least 300 kb, at least 350 kb, at least 400 kb, at least 450 kb or at least 500 kb in length.

The method of the invention can be used to obtain a plurality of polynucleic acid sequences. For example, the method of the invention can be carried out multiple times in parallel, with the result being a plurality of polynucleic acid sequences. The polynucleic acid sequences obtained by carrying out the method of the invention multiple times can then be joined together into a longer polynucleic acid sequence, for example using the method of the present invention but where N represents a polynucleic acid sequence rather than a nucleic acid sequence. This method can therefore be used to produce longer polynucleic acid sequences.

In the method of the invention, each N may be the same or a different nucleic acid sequence. The method of the invention can therefore be used for the combinatorial assembly of the same or different nucleic acid sequences. Typically, each N is a different nucleic acid sequence. However, the method of the invention can also be used to produce a polynucleic acid sequence comprising a number of nucleic acids which are the same, for example to increase the copy number of a protein-coding sequence. This embodiment of the invention is useful in the preparation of a combinatorial library of nucleic acid sequences as described herein.

The nucleic acid sequences used in the present invention can be coding or non-coding sequences. Typically, each nucleic acid sequence used in the present invention is a protein coding sequence or a regulatory or control element.

The nucleic acid sequences used in the present invention can be obtained from any suitable source. For example, the nucleic acid sequences can be synthesised for use in the invention or can be obtained from a natural source. Conveniently, the nucleic acid sequences used in the present invention can be sourced from the BioBricks™ registry of standard parts (Cambridge, Mass.; http://partsregistry.org). BioBricks™ parts are nucleic acids of defined structure and function. The method of the present invention can therefore be used to assemble existing BioBricks™ parts available from the BioBricks™ registry of standard parts.

Protein coding sequences for use in the present invention include sequences that encode proteins that are part of metabolic or other genetic pathways. Protein coding sequences for use in the present invention also include sequences that encode experimentally useful proteins, such as reporter proteins. Suitable reporter proteins for use in the present invention include coloured proteins such as lacZa, fluorescent proteins such as RFP or GFP, and proteins that confer antibiotic resistance. Reporter genes are linked to a test promoter, enabling activity of the promoter gene to be determined by detecting the presence of the reporter gene product.

For example, as described in the Examples herein, the method of the invention can be used to produce a DNA assembly in which a ribosome binding site (RBS) is inserted between a transcriptional promoter and a reporter protein, for example lacZa or mRFP1. Proper insertion of this RBS results in a complete operon for expression of the reporter protein, resulting in a phenotypic change.

Regulatory or control elements for use in the present invention include promoters, operators, repressors, ribosome-binding sites, internal ribosome entry sites (IRESs) origins of replication, enhancers, polyadenylation regions, splice donor and acceptor sites, transcriptional termination sequences, 3' UTRs and 5' UTRs.

Promoters are regions of DNA that facilitate the transcription of a particular gene by including a binding site for RNA polymerase. Promoters typically lie upstream of the gene whose transcription they control. Promoters for use in the invention include constitutive and inducible promoters.

In a first step (i), the method of the present invention comprises providing a first nucleic acid sequence N1 which has an oligonucleotide linker sequence $L1^{3'}$ at the 3'-end of the nucleic acid sequence.

In one embodiment of the invention, the first nucleic acid sequence N1 also has an oligonucleotide linker sequence $L1^{5'}$ at the 5'-end of the nucleic acid sequence.

In a second step (ii), the method of the present invention comprises providing a second nucleic acid sequence N2 which optionally has an oligonucleotide linker sequence $L2^{3}$ at the 3'-end of the nucleic acid sequence and which has an oligonucleotide linker sequence $L2^{5'}$ at the 5'-end of the nucleic acid sequence, wherein the 5'-end linker sequence $L2^{5'}$ of nucleic acid sequence N2 is complementary to the 3'-end linker sequence $L1^{3}$ of nucleic acid sequence N1. The second nucleic acid sequence N2 therefore has an oligonucleotide linker sequence $L2^{5}$ at its 5'-end, and optionally also has an oligonucleotide linker sequence $L2^{3}$ at the 3'-end of the nucleic acid sequence.

In one embodiment of the invention, the second nucleic acid sequence N2 also has an oligonucleotide linker sequence $L2^{3'}$ at the 3'-end of the nucleic acid sequence. For example, the second nucleic acid sequence N2 has an oligonucleotide linker sequence $L2^{3'}$ at the 3'-end of the nucleic acid sequence in the embodiment where the polynucleic acid sequence is of the formula $N_{\geq 3}$, i.e. wherein the polynucleic acid sequence is comprised of 3 or more nucleic acid sequences N.

The third step (iii) of the method of the present invention is optional. The third step (iii) of the method of the invention is present in the embodiment where the polynucleic acid sequence is of the formula $N_{\geq 3}$, i.e. wherein the polynucleic acid sequence is comprised of 3 or more nucleic acid sequences N.

Thus in one embodiment of the invention, in which step (iii) of the method of the invention is not present, the method of the present invention comprises:

(a) providing a first nucleic acid sequence N1 which has an oligonucleotide linker sequence $L1^{3'}$ at the 3'-end of the nucleic acid sequence;

(b) providing a second nucleic acid sequence N2 which has an oligonucleotide linker sequence $L2^{5'}$ at the 5'-end of the nucleic acid sequence, wherein the 5'-end linker sequence $L2^{5}$ of nucleic acid sequence N2 is complementary to the 3'-end linker sequence $L1^{3'}$ of nucleic acid sequence N1;

and (c) ligating said nucleic acid sequences to form said polynucleic acid sequence.

In this embodiment of the invention, the polynucleic acid sequence is of the formula $N_2$, i.e. the polynucleic acid sequence is comprised of 2 nucleic acid sequences, N1 and N2.

In some embodiments, the first nucleic acid sequence N1 also has an oligonucleotide linker sequence $L1^{5'}$ at the 5'-end of the nucleic acid sequence. In some embodiments, the second nucleic acid sequence N2 also has an oligonucleotide linker sequence $L2^{3'}$ at the 3'-end of the nucleic acid sequence. In some embodiments, the 5'-end linker sequence $L1^{5'}$ of nucleic acid sequence N1 is complementary to the 3'-end linker sequence $L2^{3'}$ of nucleic acid sequence N2. In this embodiment of the invention, the nucleic acid is circular, and is typically circular DNA.

In the optional third step (iii), the method of the present invention comprises providing one or more additional nucleic acid sequences N, wherein nucleic acid sequence N2 has an oligonucleotide linker sequence $L2^{3'}$ at the 3'-end of the nucleic acid sequence, and wherein said one or more additional nucleic acid sequences N comprises a terminal additional nucleic acid sequence NZ, and wherein each additional nucleic acid sequence N has an oligonucleotide linker sequence at its 3'-end, wherein said terminal additional nucleic acid sequence NZ optionally lacks an oligonucleotide linker sequence at its 3'-end and wherein each additional nucleic acid sequence N has an oligonucleotide linker sequence at its 5'-end, wherein for the first additional nucleic acid sequence N3 the 5'-end linker sequence $L3^{5'}$ is complementary to the 3'-end linker sequence $L2^{3'}$ of nucleic acid sequence N2 and for each second and subsequent additional nucleic acid sequence N the 5'-end linker sequence is complementary to the 3'-end linker sequence of the respective preceding additional nucleic acid sequence.

In step (iii), the 5'-end linker sequence of each second and subsequent additional nucleic acid sequence N is complementary to the 3'-end linker sequence of the respective preceding additional nucleic acid sequence. In other words, $Li^{5'}$ is complementary to $L(i-1)^{3'}$.

In some embodiments, the first nucleic acid sequence N1 also has an oligonucleotide linker sequence $L1^{5'}$ at the 5'-end of the nucleic acid sequence. In some embodiments, the terminal additional nucleic acid sequence NZ also has an oligonucleotide linker sequence $LZ^{3'}$ at the 3'-end of the nucleic acid sequence. In some embodiments, the 5'-end linker sequence $L1^{5'}$ of nucleic acid sequence N1 is complementary to the 3'-end linker sequence $LZ^{3}$ of nucleic acid sequence NZ. In this embodiment of the invention, the nucleic acid is circular, and is typically circular DNA.

In one embodiment of the invention, the method of the present invention comprises:

(i) providing a first nucleic acid sequence N1 which has an oligonucleotide linker sequence $L1^{3'}$ at the 3'-end of the nucleic acid sequence;

(ii) providing a second nucleic acid sequence N2 which has an oligonucleotide linker sequence $L2^{3'}$ at the 3'-end of the nucleic acid sequence and which has an oligonucleotide linker sequence $L2^{5}$ at the 5'-end of the nucleic acid sequence, wherein the 5'-end linker sequence $L2^{5}$ of nucleic acid sequence N2 is complementary to the 3'-end linker sequence $L1^{3'}$ of nucleic acid sequence N1;

(iii) providing a third nucleic acid sequence N3 which has an oligonucleotide linker sequence $L3^{5'}$ at the 5'-end of the nucleic acid sequence, wherein the 5'-end linker sequence $L3^{5}$ of nucleic acid sequence N3 is complementary to the 3'-end linker sequence $L2^{3'}$ of nucleic acid sequence N2;

and (iv) ligating said nucleic acid sequences to form said polynucleic acid sequence.

In this embodiment of the invention, the polynucleic acid sequence is of the formula $N_3$, i.e. the polynucleic acid sequence is comprised of 3 nucleic acid sequences, N1, N2 and N3.

In some embodiments, the first nucleic acid sequence N1 also has an oligonucleotide linker sequence $L1^{5'}$ at the 5'-end of the nucleic acid sequence. In some embodiments, the third nucleic acid sequence N3 also has an oligonucleotide linker sequence $L3^{3'}$ at the 3'-end of the nucleic acid sequence. In some embodiments, the 5'-end linker sequence $L1^{5'}$ of nucleic acid sequence N1 is complementary to the 3'-end linker sequence $L3^{3'}$ of nucleic acid sequence N3. In this embodiment of the invention, the nucleic acid is circular, and is typically circular DNA.

In a fourth step (iv), the method of the present invention comprises ligating said nucleic acid sequences to form said polynucleic acid sequence.

Typically, step (iv) of the method of the invention is carried out using DNA ligase. DNA ligase is an enzyme that links together two DNA strands that have a double-stranded break. Any type of commercially available DNA ligase can be used in the present invention. Any of the mammalian DNA ligases (DNA ligase I, DNA ligase II, DNA ligase III, DNA ligase IV) can be used in the present invention. Step (iv) of the method of the invention can alternatively be carried out using RNA ligase.

In one embodiment, step (iv) of the method of the invention is carried out using chemical ligation. Any suitable method for carrying out chemical ligation can be used, for example using cyanogen bromide as a condensing agent or using hydrogen peroxide.

In one embodiment of the invention, the nucleic acid sequences N together with their oligonucleotide linker sequences are purified immediately prior to step (iv). Any suitable method can be used to purify the nucleic acid sequences. Typically, the nucleic acid sequences are purified using DNA purification spin columns or gel extraction. For example, the part-linker pairs can be purified using the QiaQuick™ PCR purification kit (Qiagen™) or via gel electrophoresis and extraction via the QiaQuick™ gel extraction kit (Qiagen™). Many other suitable methods of purifying nucleic acid sequences will be known to the skilled person and can be used in the present invention, for example biotin-based purification methods such as biotin-streptavidin purification, high performance liquid chromatography (HPLC) and nuclease treatment that selectively destroys unbound oligonucleotides.

Once the method of the invention has been carried out to produce the polynucleic acid sequence, the polynucleic acid sequence can be transformed into suitable cells to verify that the assembly has been successful. Suitable cells include chemically competent *E. coli* (available from Invitrogen). The successful assembly can then be verified, e.g. by plating out the cells and counting coloured/colourless colonies (for the blue and red assays described in the Examples herein).

In one embodiment of the invention, each of the nucleic acid sequences N is provided with an overhang at one or both ends. In some embodiments, the nucleic acid sequences N have an overhang only at one end, either the 3'-end or the 5'-end. Typically, each nucleic acid sequence N has an overhang at both the 3'-end and the 5'-end. This embodiment of the invention is illustrated in FIGS. 6 and 7.

Typically, the overhang at one or both ends of each nucleic acid sequence is produced by digestion with one or more restriction enzymes. For example, in some embodiments of the invention one or more of the nucleic acid sequences is stored in a vector prior to use in the method of the invention, as shown in FIGS. 6 and 7. Typically, BioBricks™ parts, i.e. nucleic acids from the BioBricks™ registry (Cambridge, Mass.), are stored in this fashion. In this embodiment, a restriction enzyme is used to cut the nucleic acid sequence out from the vector in which it is stored before use in the method of the invention.

The overhang at one or both ends of the nucleic acid sequence can be palindromic or non-palindromic.

Any restriction enzyme can be used in the present invention. Suitable restriction enzymes for use in the invention include restriction enzymes that produce single-stranded overhangs. Typical restriction enzymes for use in the present invention are Type IIS restriction enzymes, which cleave at sites away from their recognition site.

Suitable restriction enzymes for use in the invention include EcoRI, SpeI, SapI, EarI and PstI.

In one embodiment, in which the nucleic acid sequence has an overhang at both ends, the overhang at the 5'-end of the nucleic acid sequence can be produced by digestion with EcoRI (restriction sites: SEQ ID NO: 28 and SEQ ID NO: 31; overhang: SEQ ID NO: 30) and the overhang at the 3'-end of the nucleic acid sequence can be produced by digestion with SpeI (restriction sites: SEQ ID NO: 29 and SEQ ID NO: 32; overhang: SEQ ID NO: 33). The overhangs produced by EcoRI and SpeI are palindromic. EcoRI and SpeI are typically used in this fashion to prepare BioBricks™ parts, i.e. nucleic acids from the BioBricks™ registry, and leave standard overhangs at the 5'-end and the 3'-end of the nucleic acid sequence.

In another embodiment, the overhang at the 5'-end of the nucleic acid sequence or at the 3'-end of the nucleic acid sequence can be produced by digestion with SapI or EarI (restriction sites: SEQ ID NO: 34, SEQ ID NO: 35, SEQ ID NO: 36, and SEQ ID NO:37). The overhangs produced by SapI and EarI are non-palindromic.

The overhangs produced by EcoRI/SpeI and SapI/EarI are shown diagrammatically in FIG. 8.

The overhangs on each nucleic acid sequence N are typically produced by digestion with the same restriction enzyme or combination of restriction enzymes. Alternatively, the overhangs on different nucleic acid sequences N can be produced using different restriction enzymes or combinations of restriction enzymes. For example, one nucleic acid sequence N can be designed to be cut by EcoRI/SpeI and another nucleic acid sequence N can be designed to be cut by EcoRI/PstI. However, in either of these embodiments, there will typically be one standard overhang on each of the nucleic acid sequences.

In one embodiment, the overhang is 3 or 4 nucleotides in length. However, the overhang can be of a different length, for example 2 nucleotides or 5, 6, 7, 8, 9 or 10 nucleotides in length.

In one embodiment, the overhang at the 3'-end of the nucleic acid sequence is the same for each nucleic acid sequence. In another embodiment, the overhang at the 5'-end of the nucleic acid sequence is the same for each nucleic acid sequence. In another embodiment, the overhang at the 3'-end of the nucleic acid sequence and the overhang at the 5'-end of the nucleic acid sequence is the same for each nucleic acid sequence. The overhang can therefore be the same or different at each end of the nucleic acid sequence.

In the embodiment in which the overhang at the 3'-end of the nucleic acid sequence or at the 5'-end of the nucleic acid sequence is the same for each nucleic acid sequence, the nucleic acid sequences can be designed such that the same overhang is produced after restriction digest, i.e. after digestion with a restriction enzyme.

In one embodiment, the present invention encompasses a library of nucleic acid sequences with appropriate overhangs ready for use in the invention.

Each nucleic acid sequence used in the method of the present invention has an oligonucleotide linker sequence at the 3'-end, at the 5'-end or at both the 3'-end and the 5'-end of the nucleic acid sequence, as described herein.

In one embodiment, the present invention encompasses a library of nucleic acid sequences together with appropriate oligonucleotide linker sequences ready for use in the invention.

The oligonucleotide linker sequences used in the present invention are typically double stranded. Typically, the oligonucleotide linker sequences are partially double stranded. That is to say, each of the 3'-end linker sequences and each of the 5'-end linker sequences used in the method of the present invention is typically partially double stranded. By "partially double stranded" is meant that either the 3'-end or the 5'-end of the linker sequence or both has an overhang. In this embodiment, each of the two strands of the 3'-end linker sequences and the 5'-end linker sequences have different numbers of nucleotides. The result of this is that each of the linker sequences has an overhang. The linker sequences can therefore be considered as being comprised of two separate single stranded oligonucleotide sequences of different lengths, with the result being that the linker sequences are partially double stranded and have one or more overhangs. This embodiment of the invention is illustrated in FIGS. 6 and 7.

In some embodiments of the invention, the overhang at one end of the nucleic acid sequence is complementary to the overhang on the 3'-end linker sequence and/or to the overhang on the 5'-end linker sequence. This embodiment of the invention is also illustrated in FIGS. 6 and 7. In these embodiments of the invention, each of the nucleic acid sequences used in the method of the invention is attached to its said 3'-end linker sequence and to its said 5'-end linker sequence by oligonucleotide annealing and ligation. In some embodiments, where the nucleic acid is DNA, ligation is carried out using DNA ligase.

In some embodiments, the oligonucleotide linker sequences used in the present invention are single stranded.

The method of the invention can also be used for the preparation of a combinatorial library of nucleic acid sequences.

According to a second aspect, the present invention therefore provides a method for the preparation of a library of polynucleic acid sequences, the method comprising simultaneously producing a plurality of different polynucleic acid sequences using the method of claim 1.

In one embodiment of the second aspect of the invention, the method for the preparation of a library of polynucleic acid sequences comprises simultaneously carrying out the method of the first aspect of the invention, i.e.

(i) providing a first nucleic acid sequence N1 which has an oligonucleotide linker sequence $L1^{3'}$ at the 3'-end of the nucleic acid sequence;

(ii) providing a second nucleic acid sequence N2 which optionally has an oligonucleotide linker sequence $L2^{3'}$ at the 3'-end of the nucleic acid sequence and which has an oligonucleotide linker sequence $L2^{5'}$ at the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1;

(iii) optionally providing one or more additional nucleic acid sequences N, wherein nucleic acid sequence N2 has an oligonucleotide linker sequence $L2^{3}$ at the 3'-end of the nucleic acid sequence, and wherein said one or more additional nucleic acid sequences N comprises a terminal additional nucleic acid sequence NZ, and wherein each additional nucleic acid sequence N has an oligonucleotide linker sequence at its 3'-end, wherein said terminal additional nucleic acid sequence NZ optionally lacks an oligonucleotide linker sequence at its 3'-end and wherein each additional nucleic acid sequence N has an oligonucleotide linker sequence at its 5'-end, wherein for the first additional nucleic acid sequence N3 the 5'-end linker sequence $L3^{5'}$ is complementary to the 3'-end linker sequence $L2^{3'}$ of nucleic acid sequence N2 and for each second and subsequent additional nucleic acid sequence N the 5'-end linker sequence is complementary to the 3'-end linker sequence of the respective preceding additional nucleic acid sequence;

and (iv) ligating said nucleic acid sequences to form said polynucleic acid sequence;

a plurality of times with different combinations of nucleic acid sequences N, thereby producing a plurality of different polynucleic acid sequences.

In this embodiment, the method of the first aspect of the invention is carried out a plurality of times simultaneously, and the output of this method is "n" distinct samples with "n" defined assemblies, i.e. the number of samples is equivalent to the number of assemblies.

In another embodiment of the second aspect of the invention, the method for the preparation of a library of polynucleic acid sequences comprises carrying out the method of the first aspect of the invention once, but carrying out the method with a mix of nucleic acid sequences for one or each of the nucleic acid sequence N1, N2 etc.

For example, for a 3-part assembly, the method of the first aspect of the invention comprises the following steps:

(i) providing a first nucleic acid sequence N1 which has an oligonucleotide linker sequence $L1^{3'}$ at the 3'-end of the nucleic acid sequence;

(ii) providing a second nucleic acid sequence N2 which has an oligonucleotide linker sequence $L2^{3'}$ at the 3'-end of the nucleic acid sequence and which has an oligonucleotide linker sequence $L2^{5'}$ at the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1;

(iii) providing a third nucleic acid sequence N3 which has an oligonucleotide linker sequence $L3^{5'}$ at the 5'-end of the nucleic acid sequence, wherein the 5'-end linker sequence $L3^{5'}$ of nucleic acid sequence N3 is complementary to the 3'-end linker sequence $L2^{3'}$ of nucleic acid sequence N2;

and (iv) ligating said nucleic acid sequences to form said polynucleic acid sequence.

In one embodiment of the second aspect of the invention, the method of the first aspect of the invention can be carried out using a random mixture of a number of different nucleic acid sequences, for example 3 different nucleic acid sequences to replace N1: N1a, N1b, and N1c. Each of the different nucleic acid sequences has the same oligonucleotide linker sequences $L1^{5'}$ and $L1^{3'}$. Each of the nucleic acid sequences N2 and N3 can also be replaced by a set of similar variants, e.g. N2a, N2b and N3a, N3b, N3c, N3d. All variants within each set have the same oligonucleotide linker sequence so that any assembly that includes one part from the N1 set, one part from the N2 set, and one part from the N3 set could form. For example, N1b, N2a, N3c is one possible assembly.

If the method of the first embodiment of the invention is carried out using 3 variants for nucleic acid sequence N1, 2 variants for nucleic acid sequence N2 and 4 variants for nucleic acid sequence N3, it can be seen that the resulting assembly will produce a library containing a random set of assemblies. In this example, there would be 24 possible assemblies that are generated in the combinatorial library.

In this embodiment, the output of this method is thus one randomized sample containing many different assemblies. This method can be used to create multiple different assemblies in a single reaction by varying the nucleic acid sequences at each position of the assembly as required.

One embodiment of the present invention is as follows.

The approach described here enables the assembly of many different pathways from a small collection of standard parts by assembling multiple parts in a single reaction step. Unlike similar "one pot" assembly approaches conducted previously, this approach requires neither synthesis of custom oligos for assembly nor that parts be assembled in a pre-defined order. By standardizing parts, it is possible to expend effort once to prepare components and then reuse them to generate many pathways in a rapid, highly parallelizable reaction.

This assembly process involves three phases: part preparation, part-linker fusion, and pathway assembly (see FIG. 1).

The part preparation is outside of the assembly cycle. Extra work is put into the design and preparation of parts in order to reduce the time required for assembly (see FIG. 2).

All parts can be stored in plasmids such that they can be cut out in a standard form. The offset cutter SapI is used as an example through this description, but this approach is by no means limited by the particular enzyme. SapI recognizes a 7 by sequence and leaves a 3 by overhang that can be anything. Parts are designed to be cut out by digestion with SapI, leaving 3 by overhangs on both ends. The 3 bp overhang on the 3'-end of the part is defined to be a standard 3 bp sequence common for all parts in this format. The 3 bp overhang on the 5'-end of the part is defined to be something other than this standard 3 bp sequence. The part sequences are all defined to not contain any extra recognition sites for SapI.

Parts are split into two regions: a short beginning region and the rest of the part. The beginning region (approximately 10 bp) is defined by oligos. The remainder of the part is stored in a plasmid as described above. When the plasmid is cut, the truncated part is released. Upon ligation with the oligos, the part is reconstituted except for an overhang on the front (e.g. 10 bp).

The process for preparing part A with defined overhangs involves:

1. Cutting the plasmid prep with SapI
2. Ligate oligos $1_A$ and $2_A$ (both 5'-phosphorylated) to the cut part
3. Also, add biotinylated oligo $5_A$ which binds to the ligation product via non-covalent base pairing (e.g. 10 bp)
4. The complex is purified via the biotin (e.g. using magnetic streptavidin beads)
5. The purified, ligated product is released by heating to break the pairing with the biotin oligo
6. Oligos $3_A$ and $4_A$ are synthesized during the construction of part A and stored in annealed form for use during the assembly Note that there may be other ways of obtaining the same final DNA structure, such as de novo DNA synthesis or PCR methods (e.g. the New England Biolabs USER™ (Uracil-Specific Excision Reagent) system). The prepared parts that are output and stored from this phase include the complete part except for a long overhang (e.g. 10 bp) on one side, and a 3 bp overhang on the other side. The short 3 bp overhang is a standard sequence and the long overhang sequence is from the part.

Designing parts in this format needs to be done once. After standardization, parts can then be reused in as many different assemblies as desired. Prepared parts are stored, along with the helper oligos, and serve as input to the assembly phases. The same part oligos can be used for all assemblies using the part. Purification and quality control during part preparation and storage ensures that the inputs to the assembly process are of the highest quality.

Note that the above description assumes that the 3 bp overhang at the end of the part is standardized. A substantially identical process is possible by standardizing the 3 bp overhang at the beginning of a part and defining oligos to complete the end of a part. The assembly process in either case is similar.

The long overhang after part preparation can be designed to form either a 5'- or 3'-overhang, unlike many other assembly methods. In addition, it is possible to mix and match both types of overhangs in an assembly without needing to know beforehand which parts will be assembled. A smart part design process would use different types of overhangs to maximize the number of parts that can be assembled in one pot.

Also described herein is the computer aided design (CAD) tools used to design the parts. The design of a part starts with the initial DNA sequence for a part, call it part A. This sequence is required to not include the recognition sequence for SapI (or any other enzyme used), in either orientation. If required, the CAD system designs oligos and a mutation strategy, such as the Quikchange mutagenesis (Stratagene) to remove these sites. This process takes into account the properties and use of the sequence, preferring silent mutations in coding regions, for example.

A (potentially modified) sequence for the complete part A is then available. In a second step, this sequence is analyzed to locate an appropriate place to truncate part A into two parts:

(1) the left most part, which will be created by the reverse complement of oligo $2_A$, (2) a truncated portion of part A, which consists of the remainder of part A. There are several considerations used by the program to locate the position of this split. (a) The three base overhang created at the left end of the truncated part A must satisfy several requirements. It must not be identical to the standard overhang forming the three base scar at the right end of every part. It must have an appropriate melting temperature, such that the ligation of annealed oligos $1_A$ and $2_A$ can be carried out efficiently. Typically, this would require a minimal GC content in the overhang. The length and melting temperature of oligo $1_A$ must be sufficient to stabilize the $1_A$ and $2_A$ annealed double strand together at the ligation temperature. The overlap of oligo $5_A$ with oligo $2_A$ must be sufficiently long and have a high enough melting temperature to stabilize the double stranded structure formed at the ligation temperature. This overlap must be sufficiently short and have low enough melting temperature to be disassociable during biotin purification of part A. The output of the algorithm is then the location of the split between the truncated part A and oligo $2_A$. This split location also determines the three base overhang at the left end of part A and the length of oligo $2_A$. The second output of the algorithm is the length of oligo $1_A$, which also determines the length of oligo $5_A$. Oligos $3_A$ and $4_A$ are then easily defined using the sequences of oligos $5_A$ and $2_A$.

The lengths of oligos $1_A$, $2_A$, and $5_A$ are determined using standard search techniques within the sequence A. It is possible that this search will fail to yield good sequences, and may require redesign of the part to satisfy the assembly process, but this is a rare event.

Another output of the algorithm is the pair of PCR primers necessary to amplify the truncated part A, including the SapI cut sites at both ends, and the three by unique left overhang, and the standard three by overhang on the right end.

In the part-linker fusion phase, parts are processed into assembly-ready parts (FIG. 3). Although assembly-ready parts depend on the desired assembly, assembly-ready parts can likely be reused in many pathway assemblies. The reactions in this phase are highly parallel and can be done in constant time (e.g. the time to assemble the pathway is independent of the number of parts contained in the pathway).

One reaction is done for every part junction that is desired. Biotin-based purification is described here, but other means of purification are of course also possible. For example, if part A and part B need to be assembled in some pathway, then the following process is performed:

1. Ligate to the prepared part A the annealed oligos $3_B$ and $4_B$ that were constructed during the part preparation phase of part B
2. The oligos for B form the standard 3 bp overhang and thus can ligate with A easily
3. $4_B$ is designed to not ligate with part A. For example, $4_B$ may have a 3'-dideoxy nucleotide or may be "missing" a base at the 3'-end
4. For purifying the correctly ligated product, $4_B$ is biotinylated
5. The complex is purified via the biotin (e.g. using magnetic streptavidin beads)
6. The purified, ligated product is released by heating to break the pairing with the biotin oligo The above process will create a molecule that contains the entirety of part A, followed by a 3 nt standard "scar" sequence, and then followed by the initial sequence of part B. We will refer to this fusion molecule as $A_B$. Both ends of this molecule will contain long overhangs matching the beginning of part A and the beginning of part B. One can imagine a scarless version of this fusion process. For example, if the 3 nt overhang were chewed back (e.g. via a nuclease) and a blunt ligation done, then the scar would disappear. We will assume for simplicity in this description that a 3 nt scar will appear between assembled parts.

The final phase is the assembly of the complete desired pathways using in vitro ligation. The process for this phase is extremely simple (FIGS. 4 and 5). As the overhangs should all match perfectly, only ligase is required in this reaction. Assume that parts A, B, Y, and Z are being assembled to form a linear DNA. Suppose parts A and Z are standard parts added at the beginning and end of all assemblies, and thus not necessarily a part of the desired pathway.

1. All of the part-linker fusions of $A_B$, $B_C$, . . . , $Y_Z$ generated from the previous step are mixed together
2. DNA ligase is added
3. Add the biotinylated oligo $5_A$ that base pairs to the front overhang of A
4. Pull out the biotin using magnetic streptavidin beads effectively purifying away anything that does not begin with part A
5. Purify away the biotinylated oligo $5_A$ by heating to break the base pairing
6. Add the biotinylated oligo $4_Z$ which base pairs to the overhang of Y
7. Pull out the biotin using magnetic streptavidin beads effectively purifying away anything that does not end with part Y
8. Purify away the biotinylated oligo $4_A$ by heating to break the base pairing
9. The biotinylated oligo is purified away by heating to break the base pairing The resulting purified fragment will contain the assembly of parts A . . . $Y_Z$. Complete dsDNA is present for the desired assembly of parts B . . . Y. Extra overhangs are present on the ends which can be blunted with a nuclease if so desired. If a circular DNA is desired, one can add a final ligation step with $Z_A$ which will complete the circle. For example, this circular DNA can then be cloned into bacteria for propagation.

The time required for the pathway assembly phase depends on the nature of the pathways to be assembled. For a subset of the parts (i.e. parts that don't have matching overhang sequences), this phase can be done in constant time, independent of the size of the pathways to be assembled. However, if some parts have matching overhangs (e.g. if a part is used multiple times in the assembly), this assembly process needs to be broken into multiple cycles such that the offending parts are assembled in different reactions before being combined.

The output of the assembly process is the purified, assembled pathway. Ultimately, sequencing will not be necessary due to the stringent quality control used during part preparation and the purification during the process. The purifications are described using biotin/streptavidin purification steps. However, other methods such as length-based (e.g. gel electrophoresis) can also be substituted.

It is possible for an assembled pathway to be used as a new part via idempotent assembly. If one wishes to use the assembly process to produce a plasmid that can itself be used as a part (i.e. contains the correct placement of SapI sites), a couple of small changes need to be made. During the part preparation phase for the first part (A), a different set of oligos that add back a SapI site instead of reconstituting part A should be used. The last part during the assembly (Z) should also contain a SapI site in the proper location. All other aspects of the assembly can remain the same.

In one embodiment, the present invention provides a method for the assembly of a polynucleic acid sequence as shown in FIG. 6.

In the part cloning phase, a part (in this case Part A) is prepared by carrying out PCR using a forward primer ($A_F$) and a reverse primer ($A_R$). The part is designed to be in a standard form, with a standard overhang at the 3'-end ($S_L$) and a standard overhang at the 5'-end ($S_P$), each of which is designed to be recognised by a particular restriction enzyme. Conveniently, the part can be cloned into a plasmid for storage before carrying out the part preparation phase.

In the part preparation phase, the plasmid containing the part is digested with one or more restriction enzymes that recognises and cuts the part at a predefined sequence, leaving standard overhangs at the 3'-end ($S_L$) and at the 5'-end ($S_P$) of the part.

In the part/linker assembly phase, the part (in this case Part A) is ligated and purified using one set of standard part oligos. These oligos bind at the 5'-end of the part. The standard part oligos include a partially double stranded linker oligonucleotide that consists of a shorter oligonucleotide ($X^1_{P2}$) that binds to the overhang $S_P$ at the 5'-end of the part and a longer oligonucleotide ($X^1_{P1}$) that binds directly to the 5'-end of the part on the strand which does not have the overhang. $X^1_{P2}$ is complementary to $X^1_{P1}$ and since $X^1_{P1}$ is longer than $X^1_{P2}$ a new overhang is created at the 5'-end of the part.

The standard part oligos also include a part purification oligo ($X^1_{PP}$) that binds to $X^1_{P2}$ and is partially complementary to $X^1_{P1}$ in the new region of overhang created when $X^1_{P2}$ binds to $X^1_{P1}$. The part purification oligo ($X^1_{PP}$) is used to purify Part A. The part purification oligo ($X^1_{PP}$) is then removed by melting, leaving the part (Part A) with the linker oligonucleotide consisting of $X^1_{P2}$ and $X^1_{P1}$ attached.

Meanwhile, Part Z, which will bind to the 5'-end of Part A, is prepared in a similar manner to Part A. Part Z also has standard overhangs at the 3'-end ($S_L$) and at the 5'-end ($S_P$) of the part.

In the part/linker assembly phase, the part (in this case Part Z) is ligated and purified using one set of standard linker oligos. These oligos bind at the 3'-end of the part. The standard linker oligos include a partially double stranded linker oligonucleotide that consists of a shorter oligonucleotide ($X^1_{L2}$) that binds to the overhang $S_L$ at the 3'-end of the part and a longer oligonucleotide ($X^1_{L1}$) that binds directly to the 3'-end of the part on the strand which does not have the overhang. $X^1_{L2}$ is complementary to $X^1_{L1}$ and since $X^1_{L1}$ is longer than $X^1_{L2}$ a new overhang is created at the 3'-end of the part. This overhang is complementary to the overhang at the 5'-end of Part A that is formed from $X^1_{P1}$.

The standard linker oligos also include a linker purification oligo ($X^1_{LP}$) that binds to $X^1_{L2}$ and is partially complementary to $X^1_{L1}$ in the new region of overhang created when $X^1_{L2}$ binds to $X^1_{L1}$. The linker purification oligo ($X^1_{LP}$) is used to purify Part Z. The linker purification oligo ($X^1_{LP}$) is then removed by melting, leaving the part (Part Z) with the linker oligonucleotide consisting of $X^1_{L2}$ and $X^1_{PL1}$ attached.

Part Z also has a set of standard part oligos, which bind at the 5'-end of the part. The standard part oligos include a partially double stranded linker oligonucleotide that consists of a shorter oligonucleotide ($X^2_{P2}$) that binds to the overhang $S_P$ at the 5'-end of the part and a longer oligonucleotide ($X^2_{P1}$) that binds directly to the 5'-end of the part on the strand which does not have the overhang. $X^2_{P2}$ is complementary to $X^2_{P2}$ and since $X^2_{P1}$ is longer than $X^2_{P2}$ a new overhang is created at the 5'-end of the part.

In the part assembly phase, the parts A and Z are ligated together. The ligation occurs by means of the complementarity of the overhangs at the 3'-end of Part Z and at the 5'-end of Part A. These overhangs are created by oligos $X^1_{L1}$ and $X^1_{P1}$ respectively. It can be seen from FIG. 6 that the linker oligos of Part Z, $X^1_{L1}$ and $X^1_{L2}$, and the part oligos of Part A, $X^1_{P2}$ and $X^1_{P1}$, together form a standard linker $X^1$. The standard linker $X^1$ is sometimes referred to herein as X1.

FIG. 6 demonstrates only the assembly of two parts, Part A and Part Z, but the method demonstrated in FIG. 6 can be used to produce an assembly with a greater number of parts using the same process. In these embodiments of the invention, standard linkers $X^2$, $X^3$, $X^4$, $X^5$, $X^6$ and so on will be formed (sometimes referred to herein as X2, X3, X4, X5, X6 and so on).

An alternative method for the assembly of a polynucleic acid sequence according to the present invention is shown in FIG. 7.

In the part cloning phase, a truncated part (in this case truncated Part A) is prepared by carrying out PCR using a forward primer ($A_F$) and a reverse primer ($A_R$). The primers are designed to produce a truncated version of Part A, lacking some of the sequence for the part, in this case the 5'-end sequence. As with the embodiment of the invention shown in FIG. 6, the truncated part is designed to be in a standard form, with a standard overhang at the 3'-end ($S_L$) and a standard overhang at the 5'-end ($A_O$), each of which is designed to be recognised by a particular restriction enzyme. Conveniently, the truncated part can be cloned into a plasmid for storage before carrying out the part preparation phase.

In the part preparation phase, the plasmid containing the truncated part is digested with one or more restriction enzymes that recognises and cuts the truncated part at a predefined sequence, leaving standard overhangs at the 3'-end ($S_L$) and at the 5'-end ($A_O$) of the truncated part.

In the part/linker assembly phase, the truncated part (in this case truncated Part A) is ligated and purified using one set of standard part oligos. These oligos bind at the 5'-end of the truncated part. The standard part oligos include a partially double stranded linker oligonucleotide that consists of a shorter oligonucleotide ($A_{P2}$) that binds to the overhang $A_O$ at the 5'-end of the truncated part and a longer oligonucleotide ($A_{P1}$) that binds directly to the 5'-end of the truncated part on the strand which does not have the overhang. $A_{P2}$ is complementary to $A_{P1}$ and since $A_{P1}$ is longer than $A_{P2}$ a new overhang is created at the 5'-end of the part.

The standard part oligos also include a part purification oligo ($A_{PP}$) that binds to $A_{P2}$ and is partially complementary to $A_{P1}$ in the new region of overhang created when $A_{P2}$ binds to $A_{P1}$. The part purification oligo ($A_{PP}$) is used to purify the truncated Part A. The part purification oligo ($A_{PP}$) is then removed by melting, leaving the truncated part (Part A) with the linker oligonucleotide consisting of $A_{P2}$ and $A_{P1}$ attached.

Meanwhile, truncated Part Z, which will bind to the 5'-end of truncated Part A, is prepared in a similar manner to truncated Part A. Truncated Part Z also has a standard overhang at the 3'-end ($S_L$). Truncated Part Z also has an overhang at the 5'-end, which may be a standard overhang ($A_O$) or some other overhang (e.g. $Z_O$).

In the part/linker assembly phase, the truncated part (in this case Part Z) is ligated and purified using one set of standard linker oligos. These oligos bind at the 3'-end of the truncated part. The standard linker oligos include a partially double stranded linker oligonucleotide that consists of a shorter oligonucleotide ($A_{L2}$) that binds to the overhang $S_L$ at the 3'-end of the truncated part and a longer oligonucleotide ($A_{L1}$) that binds directly to the 3'-end of the truncated part on the strand which does not have the overhang. $A_{L2}$ is complementary to $A_{L1}$ and since $A_{L1}$ is longer than $A_{L2}$ a new overhang is created at the 3'-end of the truncated part. This overhang is complementary to the overhang at the 5'-end of truncated Part A that is formed from $A_{P1}$.

The standard linker oligos also include a linker purification oligo ($A_{LP}$) that binds to $A_{L2}$ and is partially complementary to $A_{L1}$ in the new region of overhang created when $A_{L2}$ binds to $A_{L1}$. The linker purification oligo ($A_{LP}$) is used to purify Part Z. The linker purification oligo ($A_{LP}$) is then removed by melting, leaving the truncated part (Part Z) with the linker oligonucleotide consisting of $A_{L2}$ and $A_{PL1}$ attached.

Truncated Part Z also has a set of standard part oligos, which bind at the 5'-end of the part. The standard part oligos include a partially double stranded linker oligonucleotide that consists of a shorter oligonucleotide ($Z_{P2}$) that binds to the overhang at the 5'-end of the truncated part, which may be a standard overhang ($A_O$) or some other overhang (e.g. $Z_O$), and a longer oligonucleotide ($Z_{P1}$) that binds directly to the 5'-end of the truncated part on the strand which does not have the overhang. $Z_{P2}$ is complementary to $Z_{P1}$ and since $Z_{P1}$ is longer than $Z_{P2}$ a new overhang is created at the 5'-end of the truncated part.

In the part assembly phase, the truncated parts A and Z are ligated together. The ligation occurs by means of the complementarity of the overhangs at the 3'-end of truncated Part Z and at the 5'-end of truncated Part A. These overhangs are created by oligos $A_{L1}$ and $A_{P1}$ respectively. It can be seen from FIG. 7 that in this embodiment of the invention the linker oligos of truncated Part Z, $A_{L1}$ and $A_{L2}$, and the part oligos of truncated Part A, $A_{P2}$ and $A_{P1}$, together with truncated Part A form the complete Part A sequence.

FIG. 7 demonstrates only the assembly of two truncated parts, truncated Part A and truncated Part Z, but the method demonstrated in FIG. 7 can be used to produce an assembly with a greater number of truncated parts using the same process.

In the embodiment of the invention demonstrated in FIG. 6, the part is the nucleic acid sequence with the standard overhangs at the 3'-end and at the 5'-end. This assembly process leads to a longer scar between the parts, the scar consisting of the standard linker $X^1$.

In the embodiment of the invention demonstrated in FIG. 7, the part includes the truncated part and the accompanying linker and part oligos. This assembly process produces the non-truncated parts with a short standard scar (consisting of the overhangs at the 3'-end of each part, in this case $S_L$).

In one embodiment of the invention, the method involves preparing parts with short overhangs (typically of 3 or 4 bp) using one or more restriction enzymes. One of the short overhangs must be the same in all the parts; the other can be the same or can be different. Matching oligos are then chosen that convert the short overhangs into longer unique overhangs. Pathway assembly is then carried out using the long unique overhangs.

If the sequence present in the oligos is viewed as a component of the part (as in the embodiment demonstrated in FIG. 7), then the part is essentially truncated and then untruncated during the assembly process. However, the part sequence can alternatively be viewed as not including the oligos (as in the embodiment demonstrated in FIG. 6). In this case, the assembly process involved adding an additional sequence (the linker and part oligos) between the parts.

The present invention has the following advantages:

- All parts to be assembled are in a standard form.
- A library of such standard parts can be created and any set of those parts can be assembled in any order.
- By using an offset cutter that leaves non-palidromic overhangs, many incorrect side products arising from palindromic overhangs (e.g. formed from most restriction enzymes) are eliminated.
- No new oligos need to be synthesized during the assembly process.
- The process is extremely parallel and in the best case, requires constant time independent of the number of parts being assembled.
- The entire time for assembly can be extremely fast. An optimal assembly would only require two ligations and three biotin-based purifications.
- The entire process involves a small number of simple operations amenable to automation.
- The process does not require in vivo steps (e.g. yeast recombination), enabling the construction of DNA that might be unstable or toxic to cells.
- The process is compatible with further in vivo processing (e.g. bacterial transformation of assembled circular plasmid and parts).
- The only enzyme required in the assembly process is DNA ligase. It does not require polymerases, nucleases, recombinases, or other enzymes.
- No amplification is required, reducing the chances of errors.
- The resulting product is pure from incorrectly assembled products, eliminating the costly need for sequencing, assuming high quality input parts and oligos.
- Ligation has been shown to scale to at least 150 kb.
- Parts with similar overhangs can be assembled by splitting the last pathway assembly step into multiple cycles (unlike, for example, PCR based approaches).
- Similar parts can be assembled in one pot if they are designed appropriately. For example, there is flexibility when designing how to break a part into the oligo portion and the rest. The actual sequence of the overhang that will be ligated during the one pot assembly step is entirely determined by the oligos used. By changing the overhang (e.g. changing its length or whether it's a 5'- or 3'-overhang), similar parts can be assembled in one pot (e.g. assembling two GFP variants together).
- A small number of parts can form a large number for pathways. For example, suppose one has 5 possible promoters that one wants to test in front of each of the genes in a 5 gene pathway. There are 10 total parts (5 promoters+5 genes). The number of possible promoter-gene and gene-promoter junctions is 50, i.e. at most 50 different part-linker fusions need to be done. These 50 part-linker fusions can then be assembled into $5^5$=3125 different pathways in one pot reactions.

One embodiment of the invention is shown in Example 1. Example 1 demonstrates a 1 part assembly in which the parts are digested at the SapI restriction sites leaving overhangs that match oligos containing a ribosome binding site. When the DNA assembly reaction is successful the ribosome binding site is inserted between the promoter and the reporter protein coding sequence. This Example demonstrates self-circularization of a 1 part assembly using single stranded oligos.

Another embodiment of the invention is shown in Example 2. Accordingly, in one embodiment the present invention provides a method for the assembly of a polynucleic acid sequence from a plurality of nucleic acid sequences in which the polynucleic acid sequence is of a formula $N_{n+2}$, in which N represents a nucleic acid sequence and where n is 1, 2 or 3 and each N may be the same or a different nucleic acid sequence, wherein the method is as described in Example 2.

In some embodiments, different enzymes are used to digest the parts before the part assembly stage—EarI (Type IIS restriction enzyme) or EcoRI-SpeI (pair of traditional restriction enzymes used for BioBrick™ assembly).

In some embodiments, plasmid DNA is digested for 2-4 hours at 37° C. and not heat-inactivated. In some embodiments, the restriction digests contain a 10× reaction buffer, a 100×BSA solution, and each appropriate restriction enzyme and the reactions made to a final volume with deionized water.

In some embodiments, the oligos used are as follows.

```
std-complement:
                                     (SEQ ID NO: 1)
/5Phos/gggggagagcgcgtgt

X1-P1-EarI:
                                     (SEQ ID NO: 2)
/5Phos/cggacacgcgctctcccccacactctcacact

X1-L1-EarI:
                                     (SEQ ID NO: 3)
/5Phos/gccacacgcgctctcccccagtgtgagagtgt

X2-P1-EarI:
                                     (SEQ ID NO: 4)
/5Phos/cggacacgcgctctcccccaggatggtaggat

X2-L1-EarI:
                                     (SEQ ID NO: 5)
/5Phos/gccacacgcgctctcccccatcctaccatcct

X3-P1-EarI:
                                     (SEQ ID NO: 6)
/5Phos/cggacacgcgctctcccccaattggggttggt

X3-L1-EarI:
                                     (SEQ ID NO: 7)
/5Phos/gccacacgcgctctcccccaccaaccccaatt

X4-P1-EarI:
                                     (SEQ ID NO: 8)
/5Phos/cggacacgcgctctcccccgattacaccggag

X4-L1-EarI:
                                     (SEQ ID NO: 9)
/5Phos/gccacacgcgctctccccccctccggtgtaatc

X1-P1-SpeI:
                                    (SEQ ID NO: 10)
/5Phos/ctagacacgcgctctcccccacactctcacact

X1-L1-EcoRI:
                                    (SEQ ID NO: 11)
/5Phos/aattacacgcgctctcccccagtgtgagagtgt

X2-P1-SpeI:
                                    (SEQ ID NO: 12)
/5Phos/ctagacacgcgctctcccccaggatggtaggat

X2-L1-EcoRI:
                                    (SEQ ID NO: 13)
/5Phos/aattacacgcgctctcccccatcctaccatcct

X3-P1-SpeI:
                                    (SEQ ID NO: 14)
/5Phos/ctagacacgcgctctcccccaattggggttggt

X3-L1-EcoRI:
                                    (SEQ ID NO: 15)
/5Phos/aattacacgcgctctcccccaccaaccccaatt

X4-P1-SpeI:
                                    (SEQ ID NO: 16)
/5Phos/ctagacacgcgctctcccccgattacaccggag

X4-L1-EcoRI:
                                    (SEQ ID NO: 17)
/5Phos/aattacacgcgctctcccccctccggtgtaatc
```

These oligos are named based on FIG. 6, e.g. X3-P1-EcoRI is the first part oligo for the third standard linker that is designed to be complementary to the overhang generated by an EcoRI digest. All part-linker oligos have a common second stranded oligo (std-complement).

In some embodiments, for EarI-digested parts, a common 5'-overhang of ggc on the 3'-end and ccg on the 5'-end of each part is used.

In some embodiments, oligo annealing and ligation to the restriction digest fragments is performed in a single reaction vessel. An appropriate set of linker oligos can be chosen for each assembly. The phase 1 and 2 (part preparation and part/linker assembly) steps can be combined. For example, for a 3-part assembly using EarI digested parts, the oligo linker set X1 can be chosen for the first part, X2 for the second part, and X3 for the third part. The first part is ligated to the oligos std-complement, X1-P1-EarI, and X2-L1-EarI. The second part is ligated to the oligos std-complement, X2-P1-EarI, and X3-L1-EarI. The third part is ligated to the oligos std-complement, X3-P1-EarI, and X1-L1-EarI.

An initial reaction mix of restriction digest, the appropriate part and linker oligos, together with the complementary oligo (std-complement), 10×T4 DNA ligase buffer (New England Biolabs, MA) and water can be heated to 65° C. in a thermocycler (Eppendorf) and the temperature ramped down to room temperature over 10 min. T4 DNA ligase (New England Biolabs, MA) and the same restriction enzymes used in the digests can then be added to the reactions. The reactions can then be incubated at 4° C. for 12 hours.

The part-linker pairs can then be purified, typically using a QiaQuick™ PCR purification kit (Qiagen™) or via gel electrophoresis and extraction via a QiaQuick™ gel extraction kit (Qiagen™).

The purified part-linker DNA for the two, three, or four parts to be assembled can then be combined in a pathway assembly reaction. Each part-linker pair can be mixed with 10×T4 DNA ligase buffer (New England Biolabs) and brought to a final volume by the addition of deionized water. The reactions can be heated and cooled as described above. Again T4 DNA ligase (New England Biolabs) and each of restriction enzymes used previously can be added and the reactions incubated at room temperature for 30 min. These can all be derived from BioBricks™ parts. Names refer to the BBa_(BioBrick™ alpha) group of parts found at http://partsregistry.org. For assembly using EcoRI/SpeI, the parts can be used as is. For assembly with EarI, the parts can first be moved in a standard way into a standard EarI conversion plasmid.

The EarI conversion plasmid can be constructed by digestion of a plasmid, such as pSB1C3 or pSB1T3 with EcoRI/PstI and ligating in the oligos:

```
                                    (SEQ ID NO: 18)
aattgctcttcgccgtctagaggatccctgcagcccgaagagcatgca

                                    (SEQ ID NO: 19)
tgctcttcgggctgcagggatcctctagacggcgaagagc
```

This conversion plasmid can then be cloned and sequenced verified.

For conversion of BioBrick™ parts into EarI-compatible parts, both the conversion plasmid and the BioBrick™ parts can be digested with XbaI/PstI. The BioBrick™ part can be ligated into the conversion plasmid and correct clones were screened and sequence verified using standard methods. After verification, these parts can become suitable as input to the assembly process with an EarI digest leaving standard 3 nucleotide 5'-overhangs (ggc on the 3'-end and ccg on the 5'-end).

The parts used can be those shown in schematic form in FIG. 10.

Preferred features of the second aspect of the invention are as described for the first aspect mutatis mutandis.

The invention will now be further described by way of reference to the following Examples and Figures which are provided for the purposes of illustration only and are not to be construed as limiting on the invention. Reference is made to a number of Figures, in which:

FIG. 1 is a schematic diagram of the method of the present invention. In phase 1, the parts and linkers are prepared. In phase 2, parts are ligated to appropriate linkers based on the desired pathway assemblies. In phase 3, all parts are ligated together. In this example, there are 3 parts being assembled: part A, part B and the plasmid backbone. Depending on the ligation method used, the assembly may leave a standard scar sequence between the parts (e.g. 3 bp).

FIG. 2 is a schematic diagram of the part preparation phase of one embodiment of the invention. Parts are prepared to have overhangs and are stored with a set of oligos associated with the part. The overhang at the 3'-end of Part A (truncated) is a standard 3 bp sequence common to all parts in a library. The biotinylated oligo $5_A$ can be used for purifying the part. The biotin is represented by the circle. Oligos $3_A$ and $4_A$ are stored for use during the assembly process.

Figure 1:
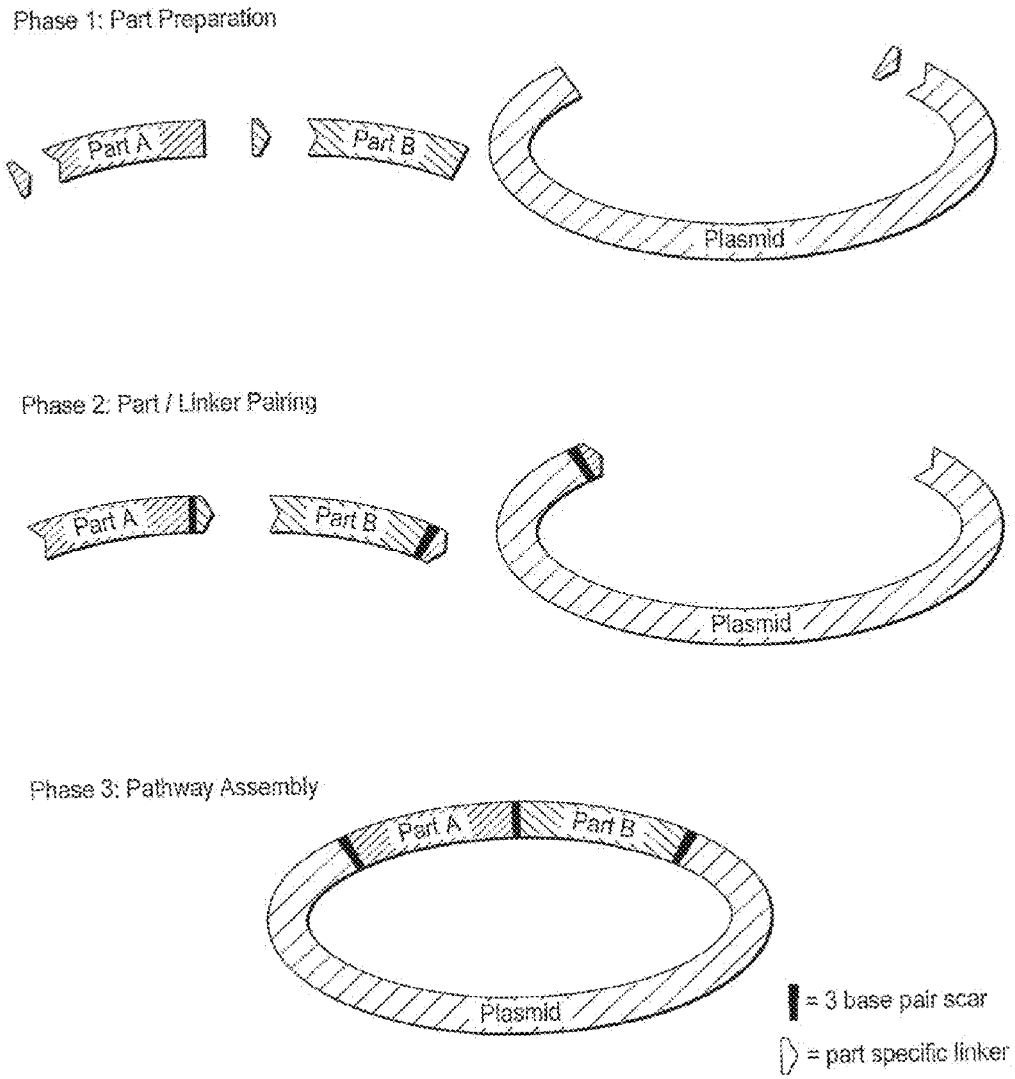
Figure 2:
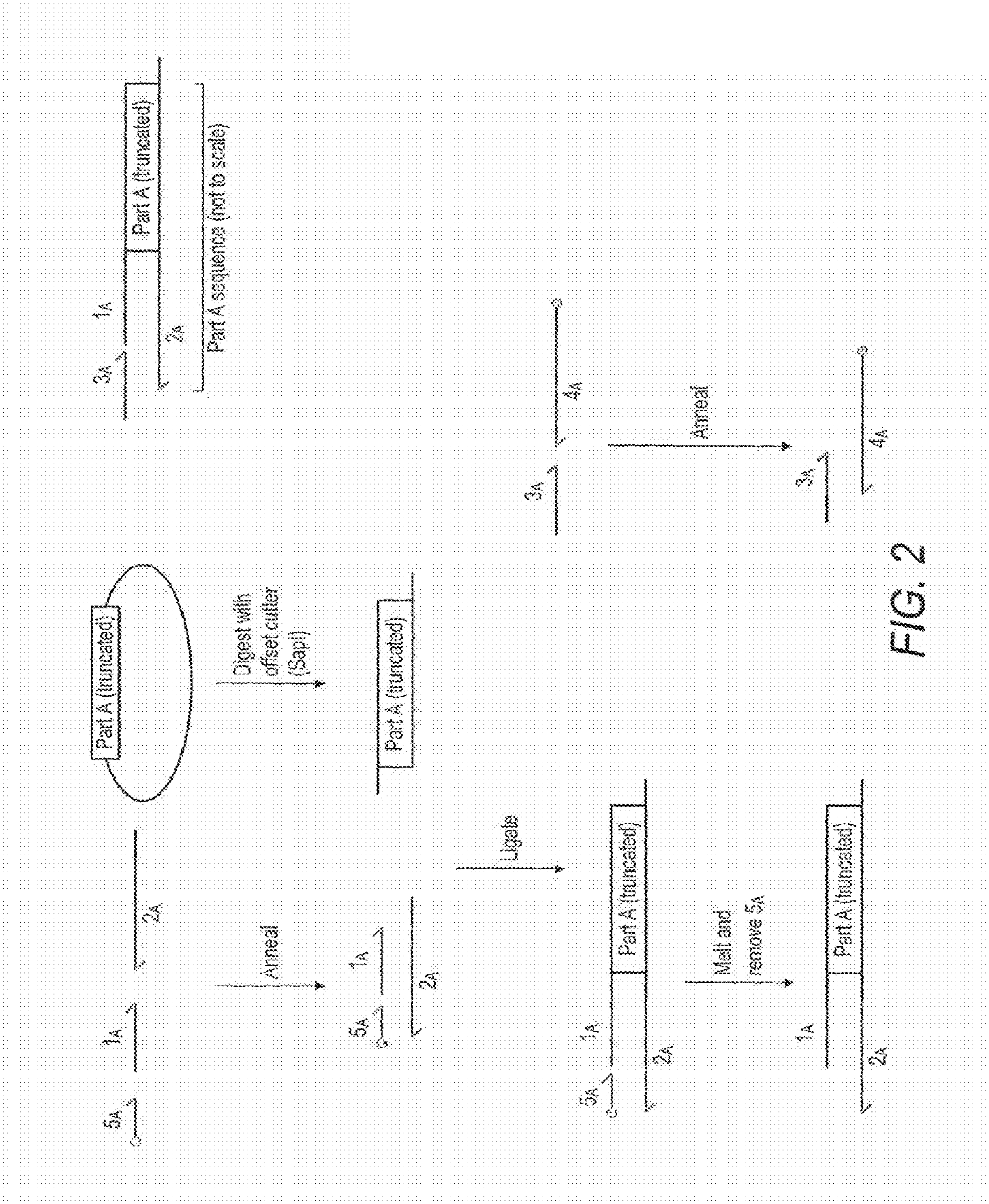
Figure 3:
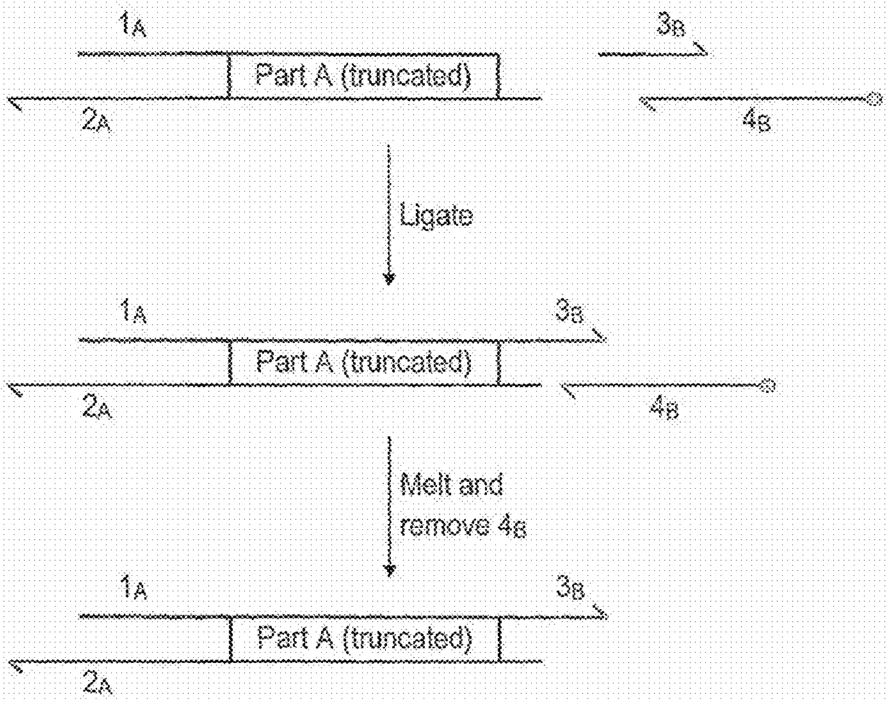
FIG. 3 is a schematic diagram of the part-linker fusion phase of one embodiment of the invention. In the part-linker fusion phase, part A is ligated with oligos for the next part B.
Figure 4:
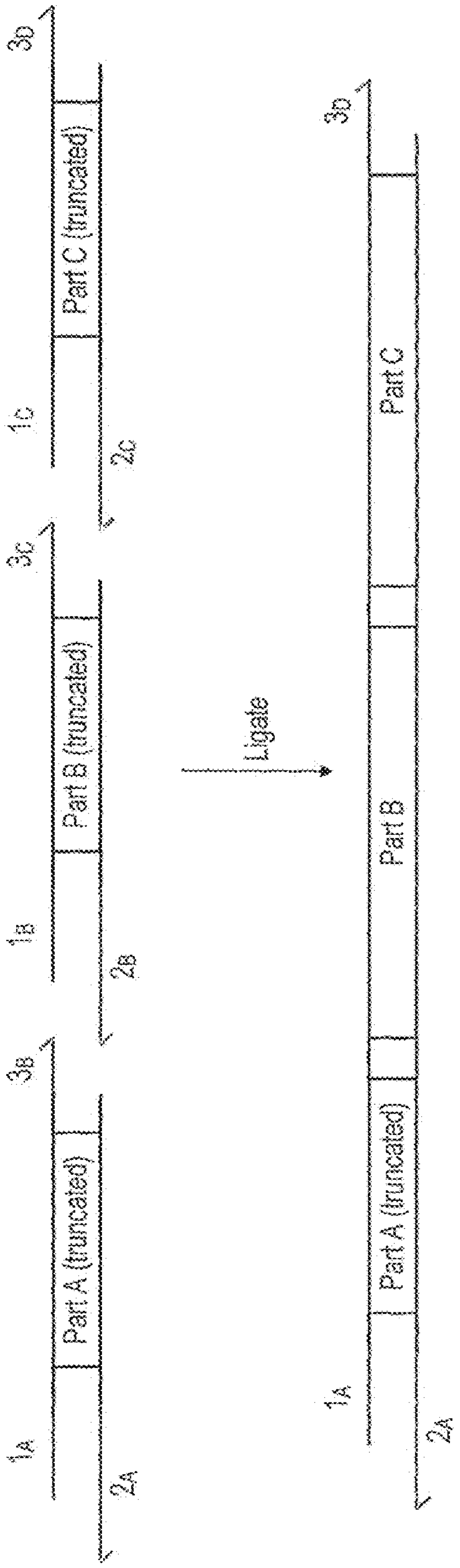
FIG. 4 is a schematic diagram of the pathway assembly phase of one embodiment of the invention. In the pathway assembly phase, part-linker fusions are ligated together.
Figure 5:
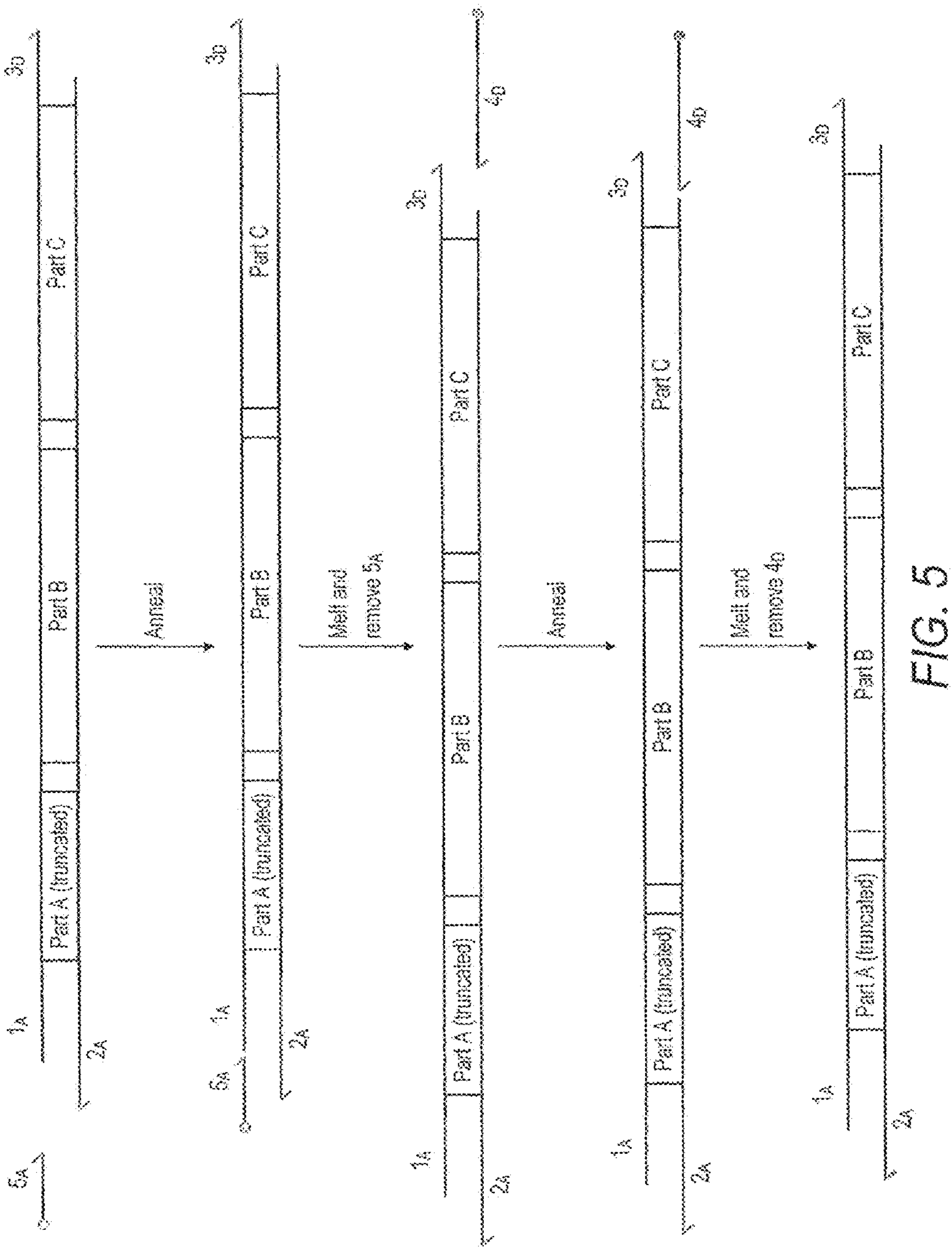

FIG. 5 is a schematic diagram of the purification of the final assembly in one embodiment of the invention. The final assembly can be purified via biotinylated oligos ($5_A$ and $4_D$). The biotin is represented by the circle.

Figure 6:
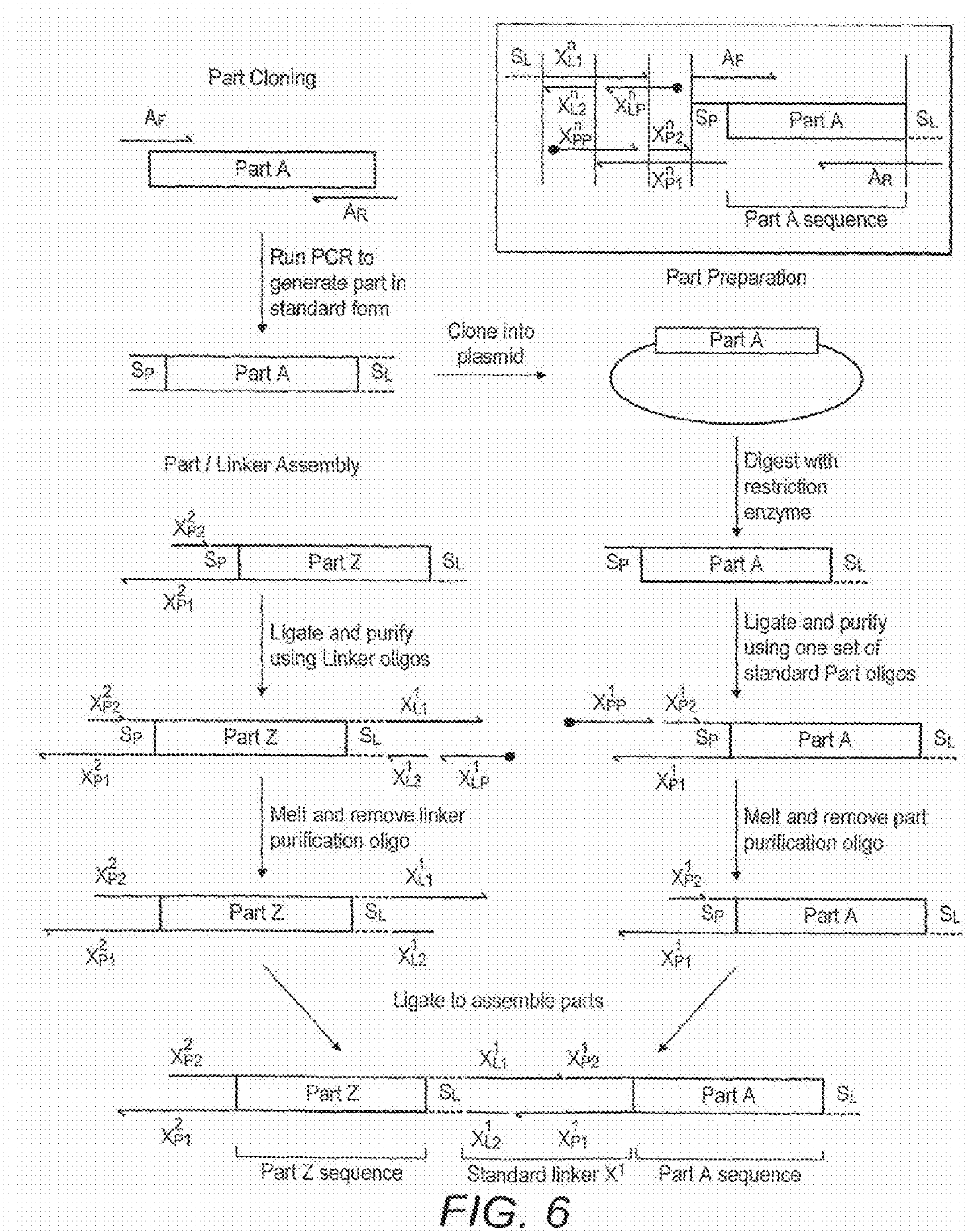

FIG. 6 is a schematic diagram of a part-linker DNA assembly scheme using partially double-stranded oligonucleotide linkers.

Figure 7:
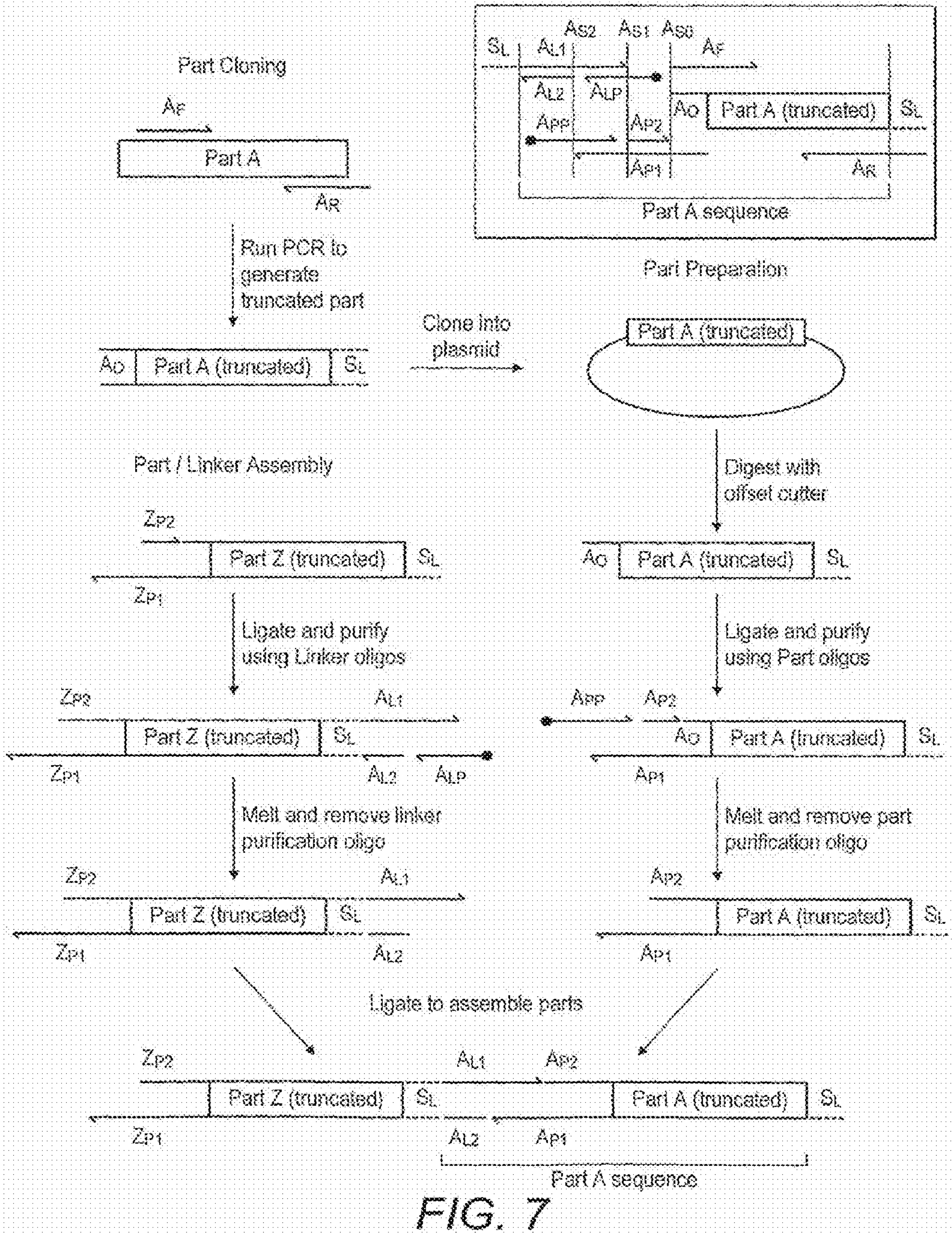

FIG. 7 is a schematic diagram of a part-linker DNA assembly scheme using partially double-stranded oligonucleotide linkers and truncated parts.

Figure 8A:
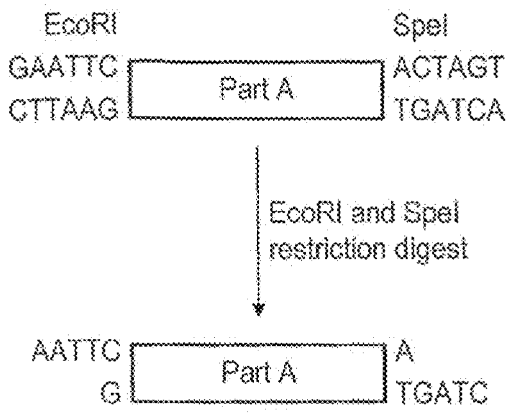
Figure 8B:
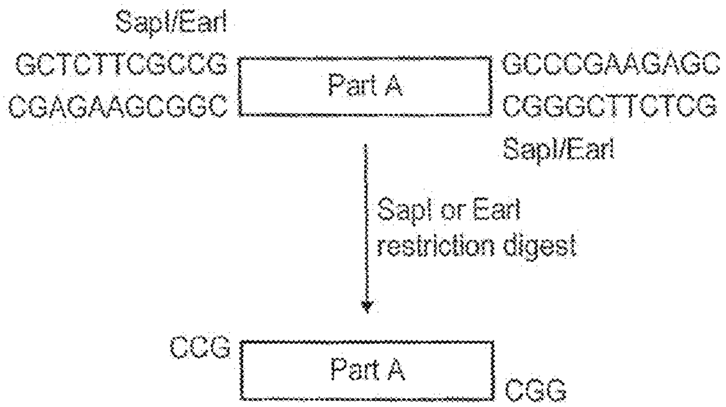

FIG. 8 shows the expected flanking sequences (overhangs) on parts following digest with (A) EcoR1/Spe1 and (B) SapI/EarI. It can be seen that the parts prepared using EcoR1/Spe1 have standard 4-bp overhangs, whilst the parts prepared using SapI/EarI have standard 3-bp overhangs.

Figure 9A:
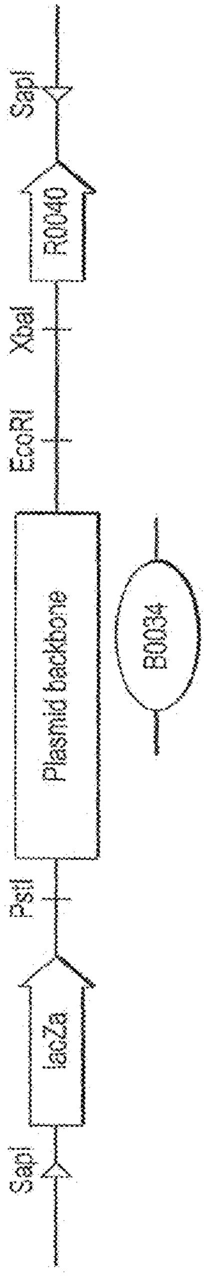
Figure 9B:
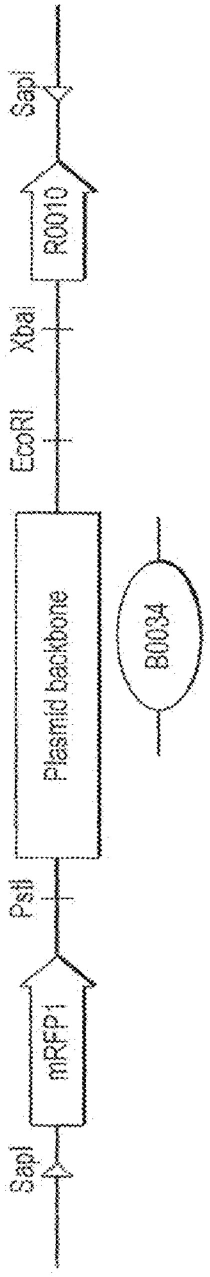

FIG. 9 is a schematic diagram of the parts designed for the blue (A) and red (B) colony assays described in Example 1. The parts are digested at the SapI restriction sites leaving overhangs that match oligos containing a ribosome binding site (B0034). When the DNA assembly reaction is successful the ribosome binding site (B0034) is inserted between the promoter (R0040 or R0010) and the reporter protein coding sequence (lacZa or mRFP1).

Figure 10:
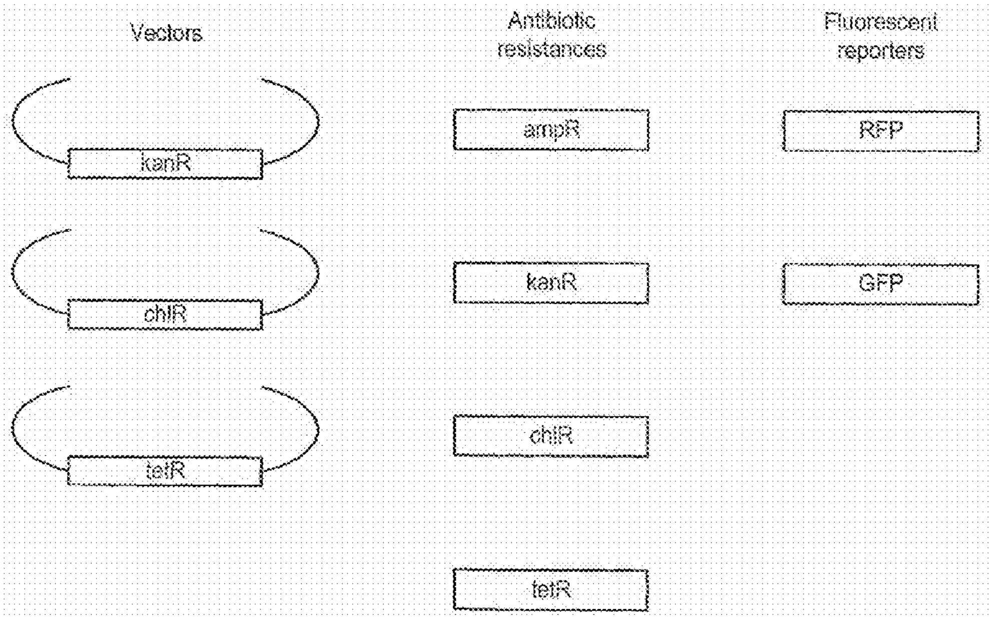

FIG. 10 is a schematic diagram of the parts used in Example 2. The parts are vector parts (kanR, chlR and tetR, referred to in Example 2 as pSB1K3, pSB1C3 and pSB1T3 respectively), antibiotic resistance parts (ampR, kanR, chlR and tetR, referred to in Example 2 as P1002, P1003, P1004 and P1005 respectively) and fluorescent reporters (RFP and GFP, referred to in Example 2 as J04450 and I7101 respectively). The parts were prepared with linkers to fill a position (1, 2, 3 or 4) in the two, three or four part assembly ordering.

Figure 11:
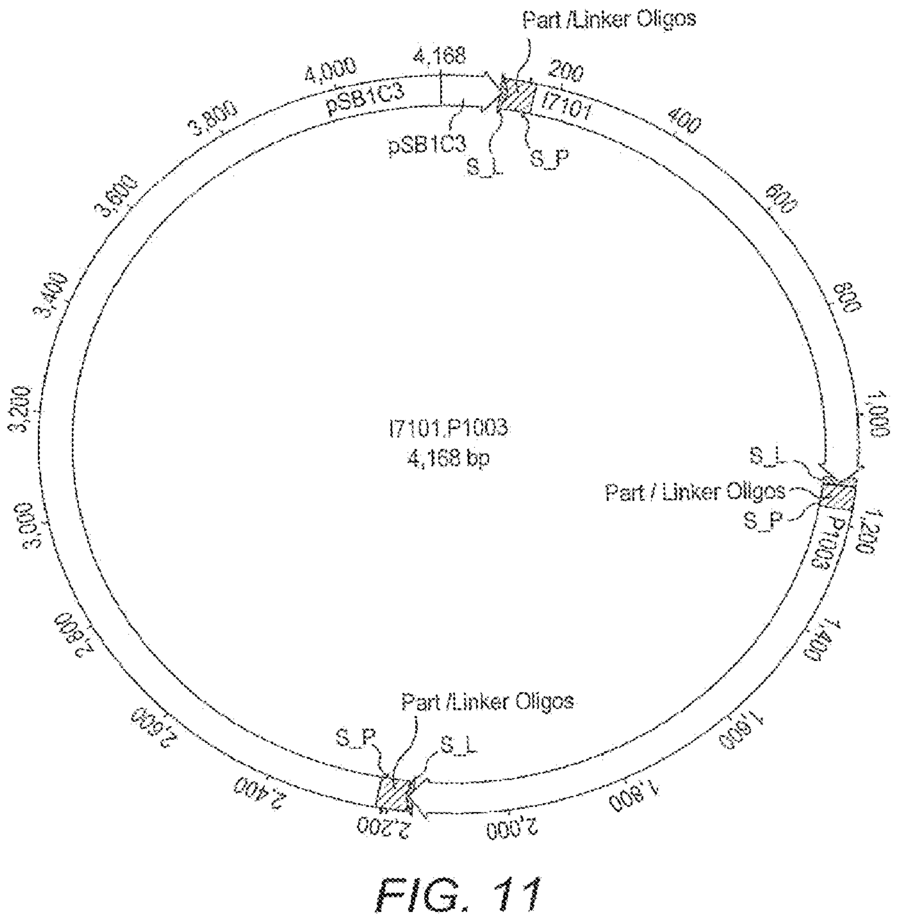

FIG. 11 is a plasmid map of the 3 part assembly pSB1C3.I7101.P1003 described in Example 2.

Figure 12:
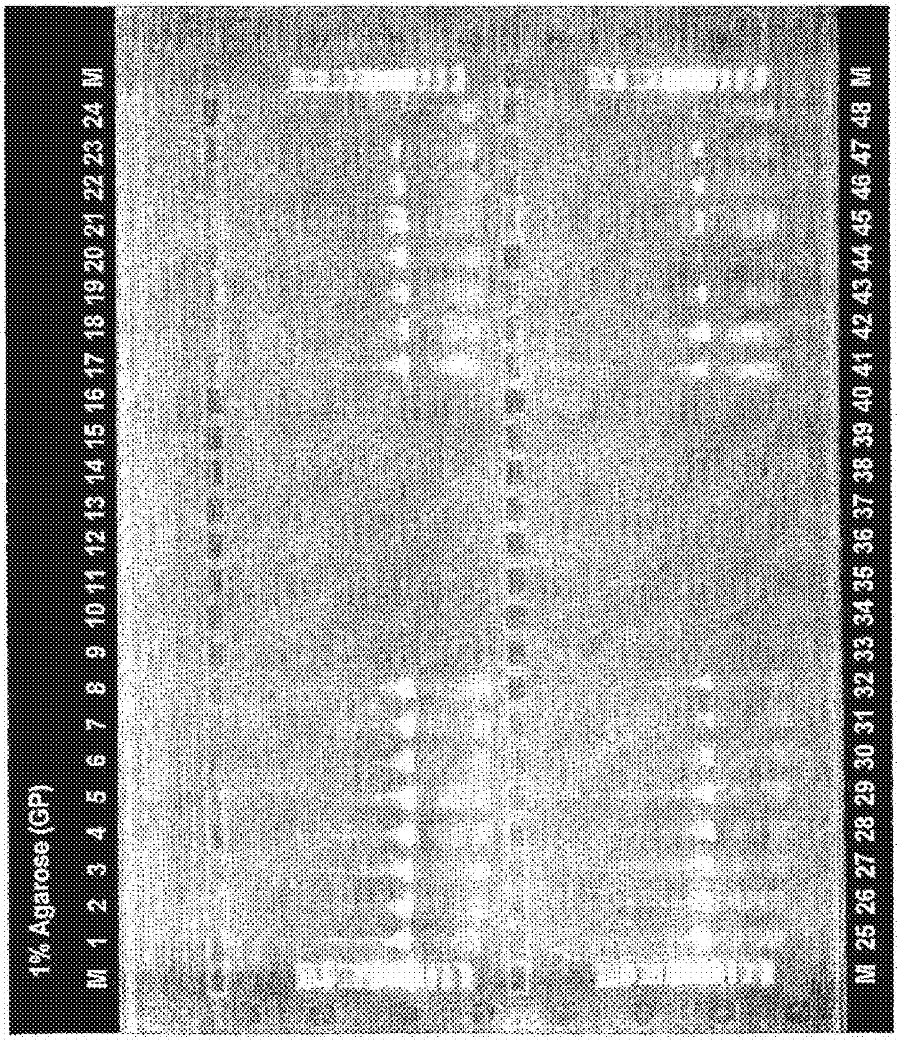

FIG. 12 is a gel that shows the verification of one correct junction for a BioBrick™-based 3-part assembly using EcoRI/SpeI. Each lane corresponds to a PCR product derived from a different colony. Lanes 1-8 are nucleic acid fragment pSB1C3.P1003.J04450. Lanes 17-24 are nucleic acid fragment pSB1C3.P1005.J04450. Lanes 25-32 are nucleic acid fragment pSB1T3.P1003.J04450. Lanes 41-48 are nucleic acid fragment pSB1T3.P1004.J04450. Lanes 9-16 and 33-40 are empty. All M lanes contain 1 μg of NEB 2-log DNA ladder.

Figure 13:
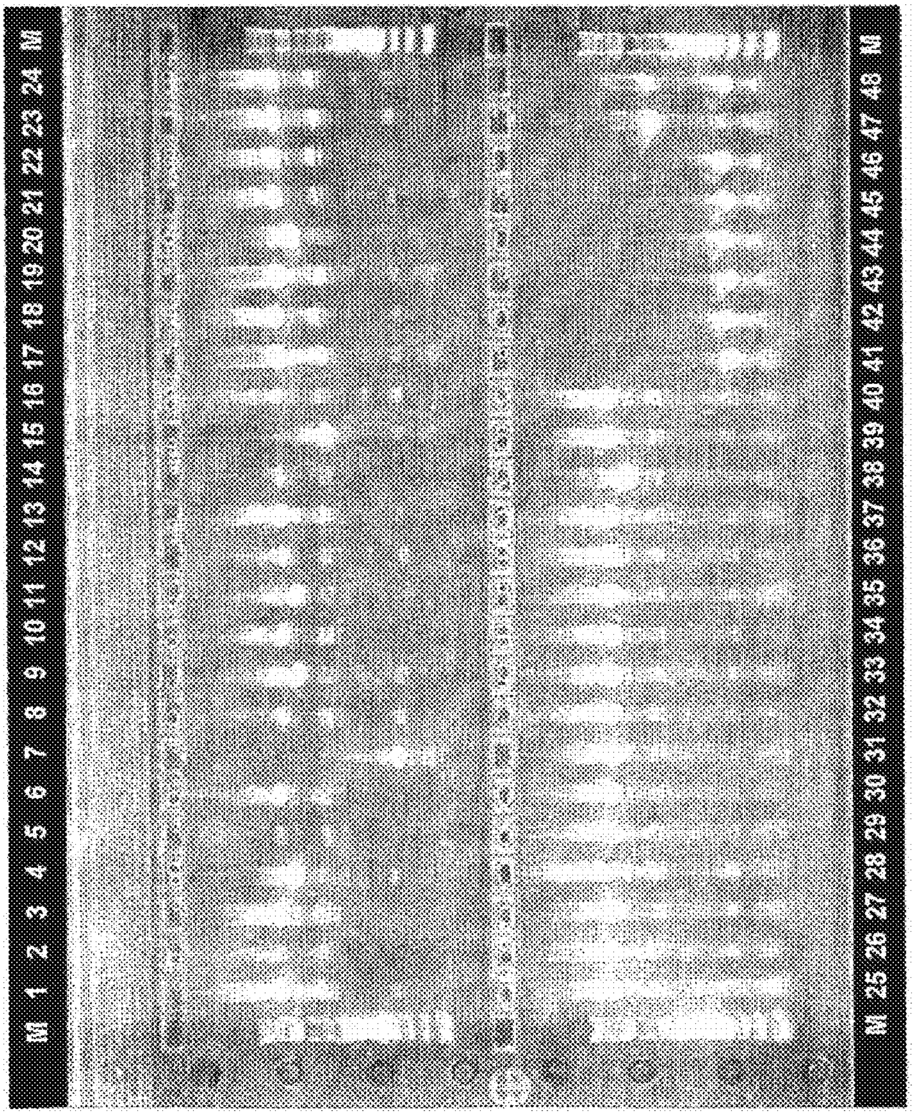

FIG. 13 is a gel that shows the results of the analysis of the 4-part assemblies summarized in Table 3. Table entries for construct 1 (4-part) refer in sequence to lanes 1, 3, 5, 7, 9, 11, 13, 15, 2, 4, 6, 8, 10, 12, 14, and 16. Table entries for construct 2 (4-part) refer in sequence to lanes 17, 19, 21, 23, 18, 20, 22, and 24. Table entries for construct 3 (4-part) refer in sequence to lanes 25, 27, 29, 31, 33, 35, 37, 39, 26, 28, 30, 32, 34, 36, 38, and 40.

Figure 14:
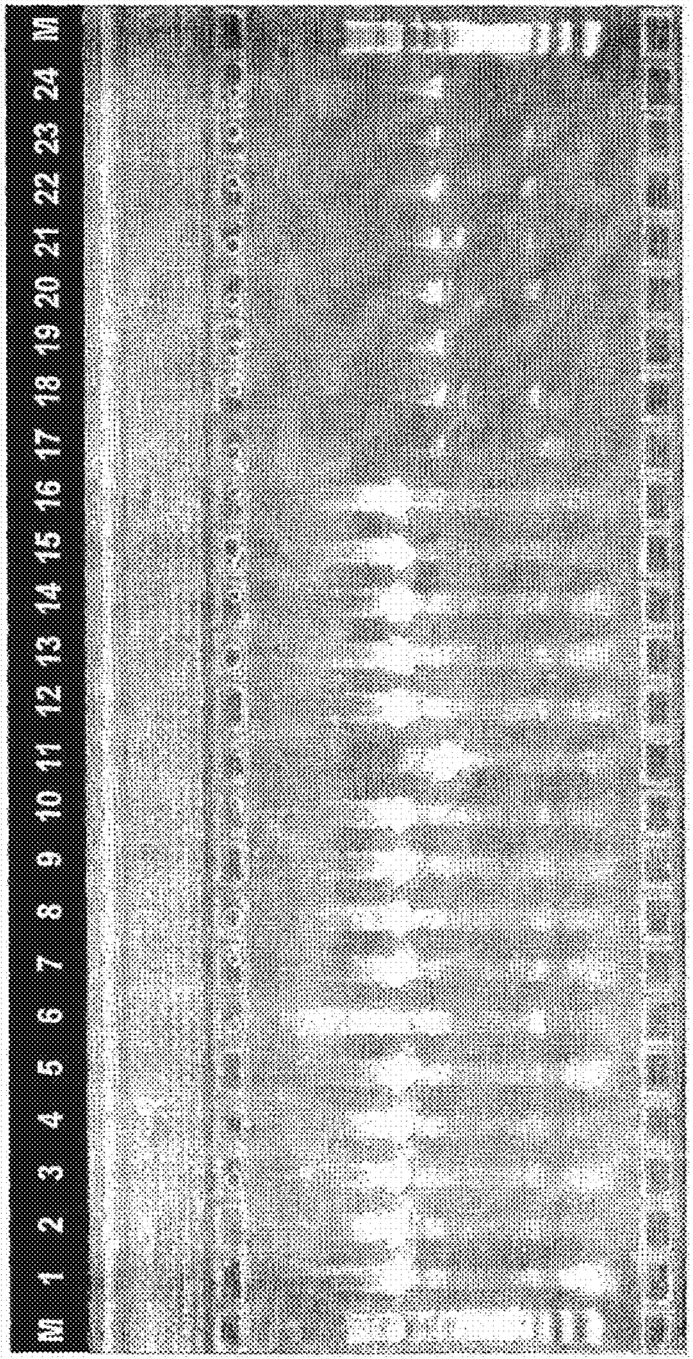

FIG. 14 is a gel that shows the results of the analysis of one of the 3-part assemblies summarized in Table 3. Table entries for construct 4 (3-part) refer in sequence to lanes 1, 3, 5, 7, 9, 11, 13, and 15. Lanes 17 through 24 show template free PCR reactions.

Figure 15:
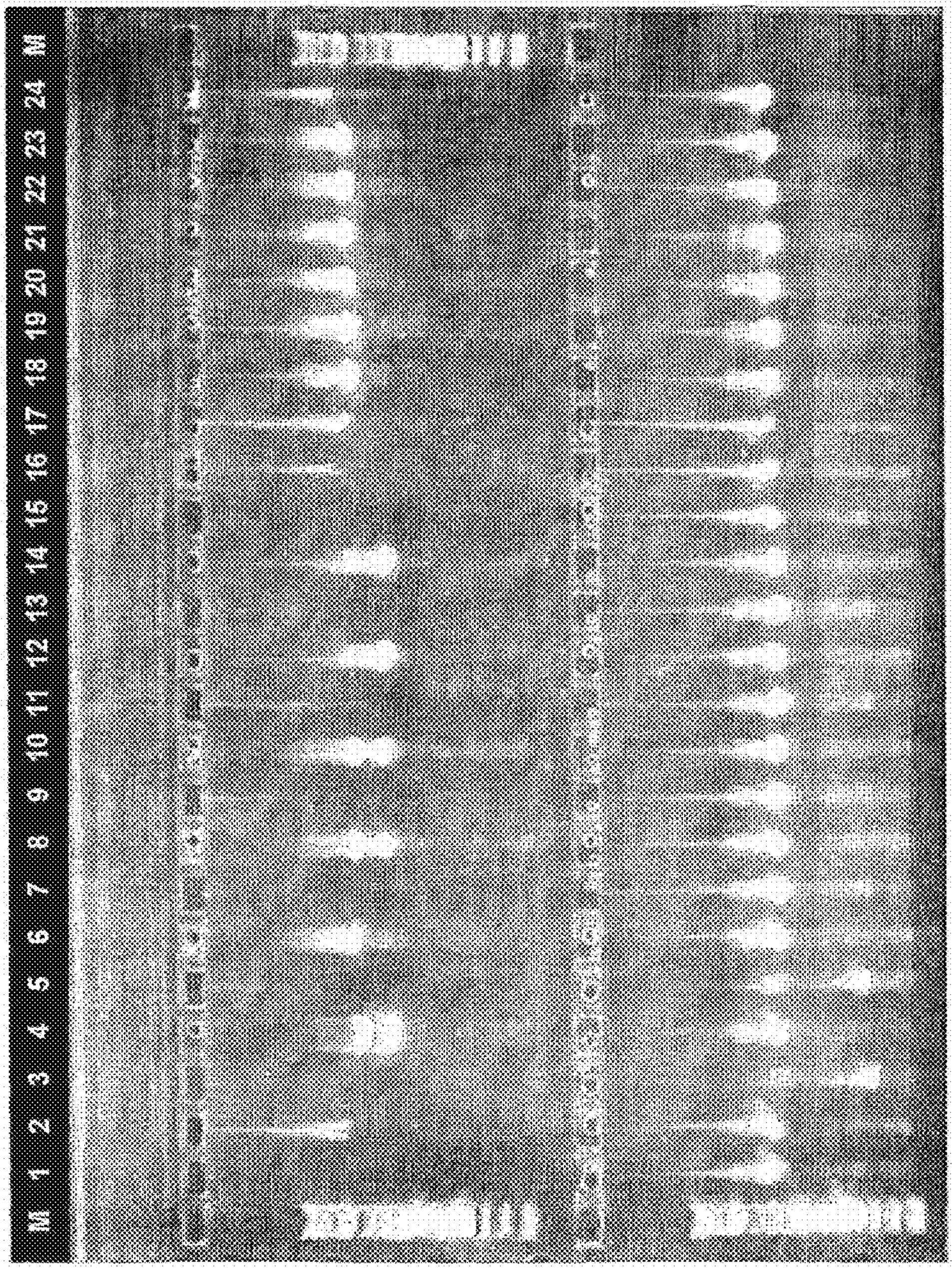

FIG. 15 is a gel that shows the results of the analysis of two of the 3-part assemblies and the 2-part assemblies summarized in Table 3. Table entries for construct 5 (3-part) refer in sequence to lanes 2, 4, 6, 8, 10, 12, 14, and 16. Table entries for construct 6 (3-part) refer in sequence to lanes 17, 19, 21, 23, 18, 20, 22, and 24. Table entries for construct 7 (2-part) refer in sequence to lanes 25, 27, 29, 31, 33, 35, 37, and 39. Table entries for construct 8 (2-part) refer in sequence to lanes 26, 28, 30, 32, 34, 36, 38, and 40. Table entries for construct 9 (2-part) refer in sequence to lanes 41, 43, 45, 47, 42, 44, 46, and 48.

Figure 16A:
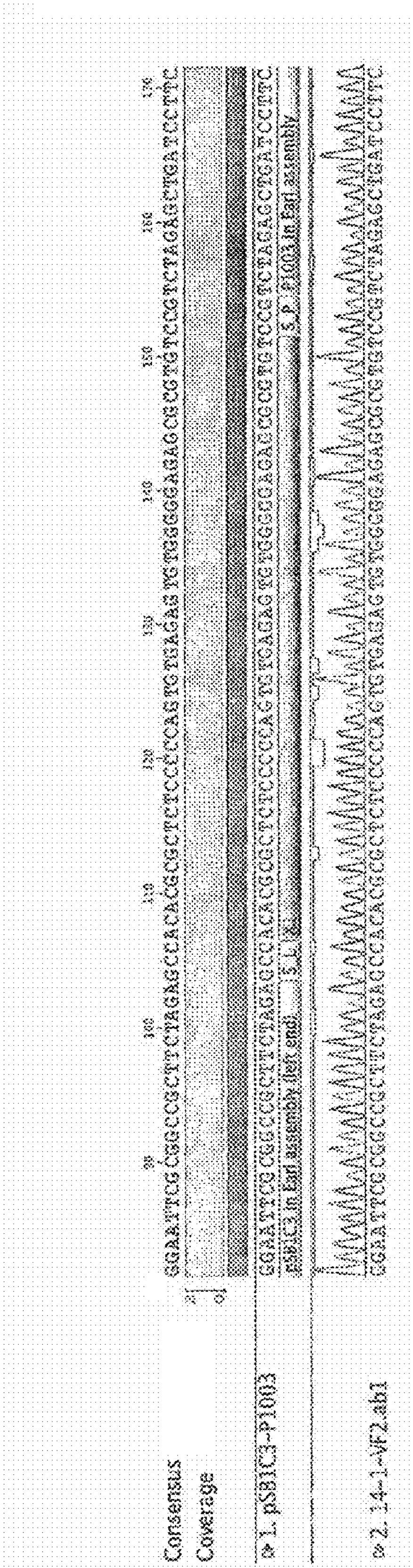
Figure 16B:
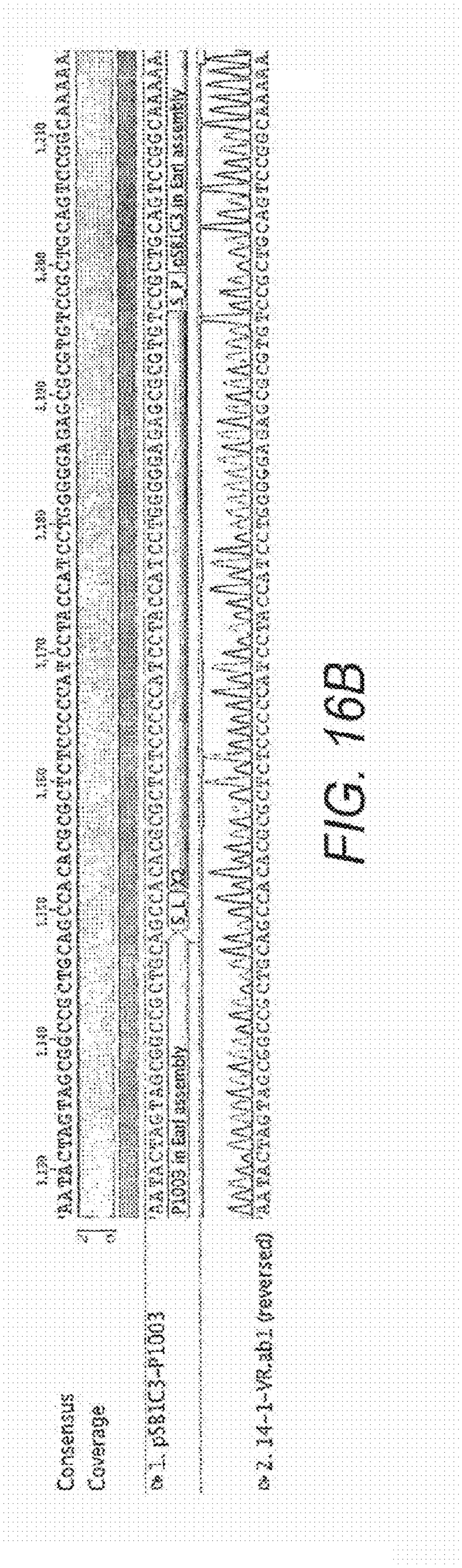

FIG. 16 shows representative sequence analysis at the part junctions for construct 9 (2 parts; pSB1C3.P1003). FIG. 16A shows the sequence of the standard part/linker sequence X1 between pSB1C3 and P1003 (SEQ ID NO: 38) and FIG. 16B shows the sequence of the standard part/linker sequence X2 between P1003 and pSB1C3 (SEQ ID NO: 39).

Figure 17A:
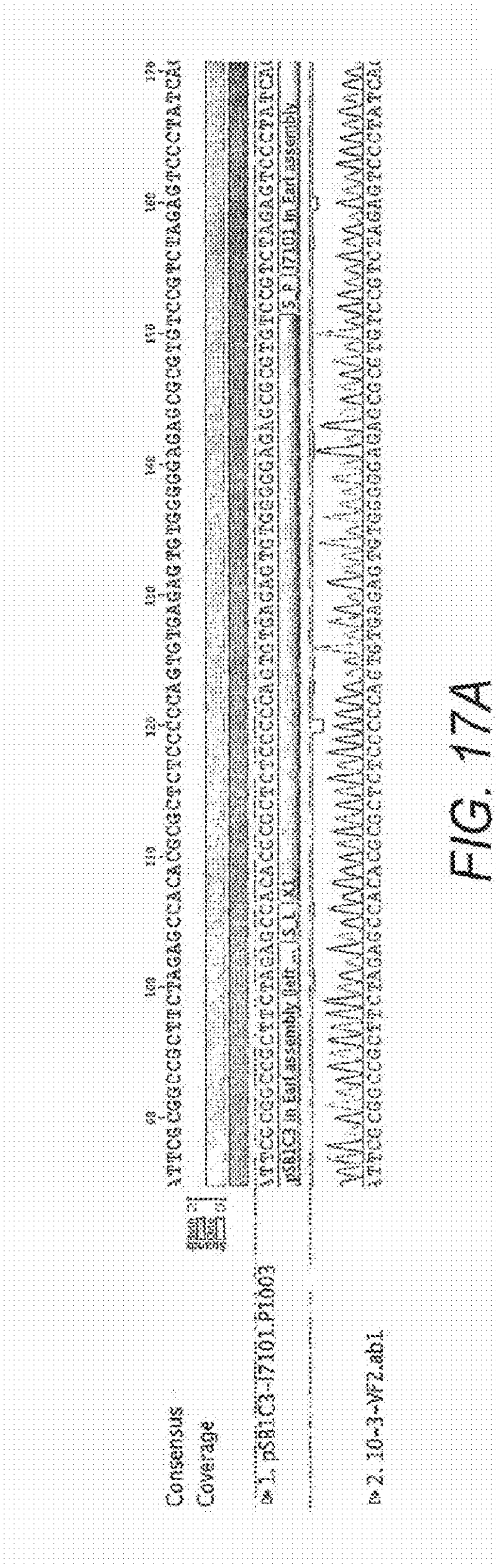
Figure 17B:
Figure 17C:
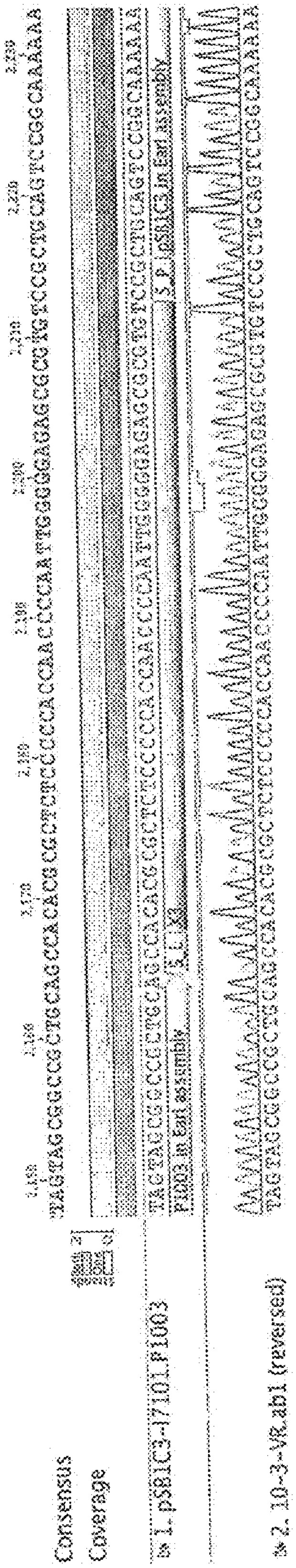
Figure 18A:
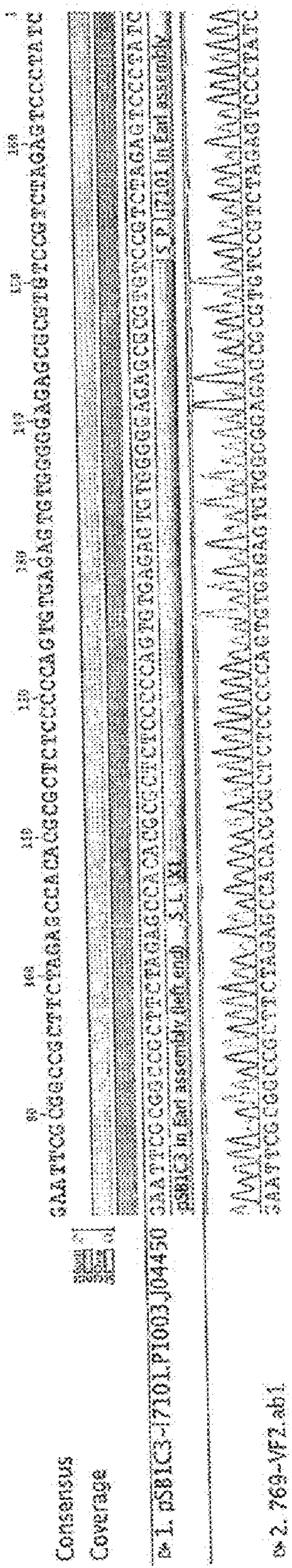
Figure 18B:
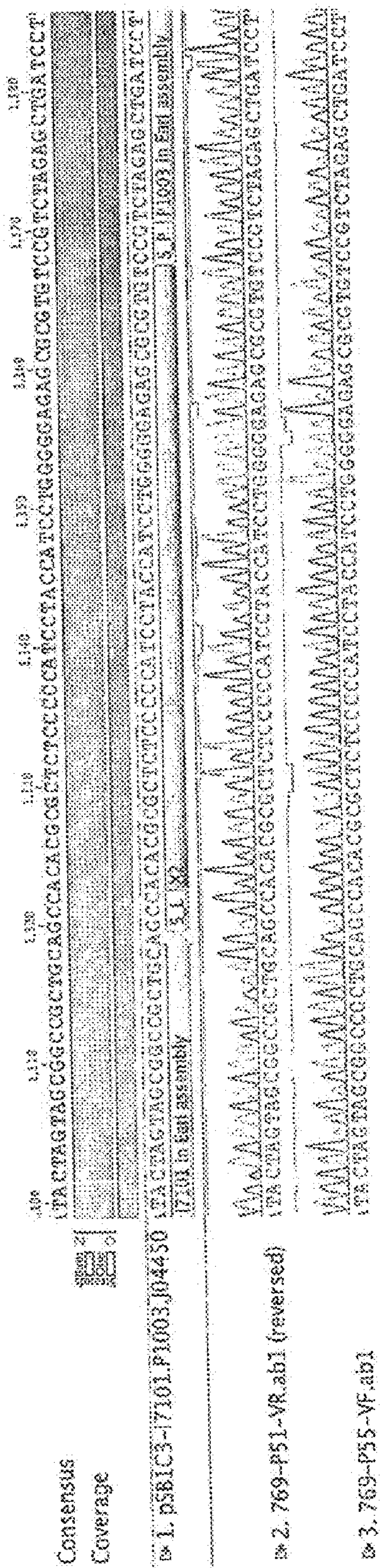
Figure 18C:
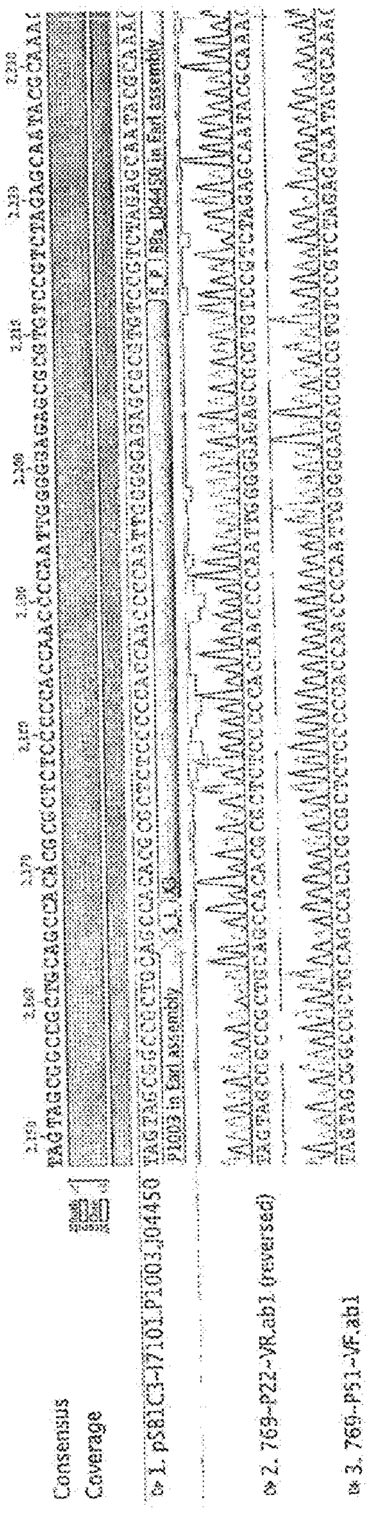
Figure 18D:
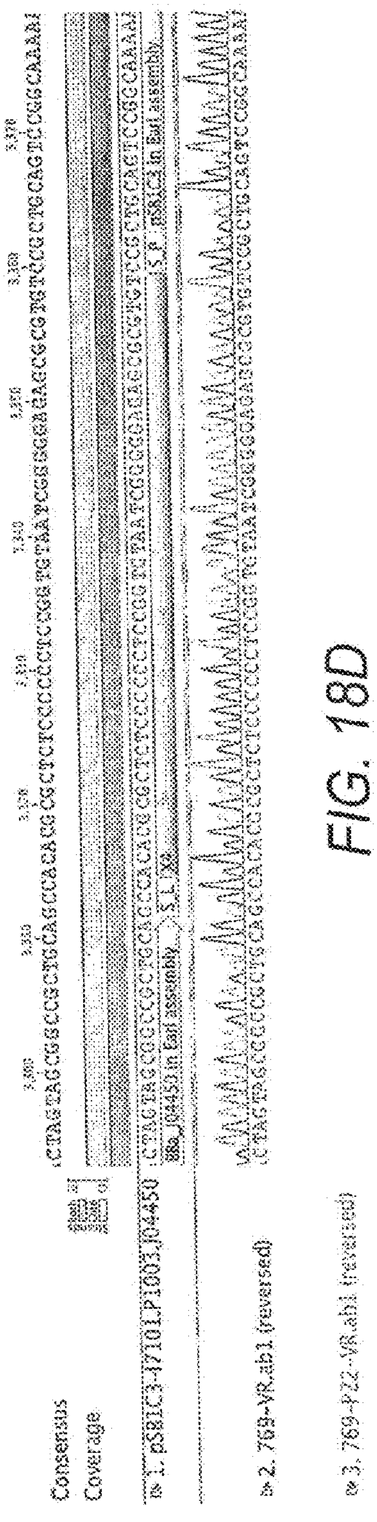

FIG. 17 shows representative sequence analysis at the part junctions for construct 5 (3 parts; pSB1C3J7101.P1003). FIG. 17A shows the sequence of the standard part/linker sequence X1between pSB1C3 and 17101 (SEQ ID NO: 40), FIG. 17B shows the sequence of the standard part/linker sequence X2 between 17101 and P1003 (SEQ ID NO: 41), and FIG. 17C shows the sequence of the standard part/linker sequence X3between P1003 and pSB1C3 (SEQ ID NO: 42).

FIG. 18 shows representative sequence analysis at the part junctions for construct 2 (4 parts; pSB1C3.17101.P1003.J04450). FIG. 18A shows the sequence of the standard part/linker sequence X1between pSB1C3 and 17101 (SEQ ID NO: 43), FIG. 18B shows the sequence of the standard part/linker sequence X2 between 17101 and P1003(SEQ ID NO: 44), FIG. 18C shows the sequence of the standard part/linker sequence X3between P1003 and J04450 (SEQ ID NO: 45), and FIG. 18D shows the sequence of the standard part/linker sequence X4between J04450 and pSB1C3 (SEQ ID NO: 46).

Figure 19A:
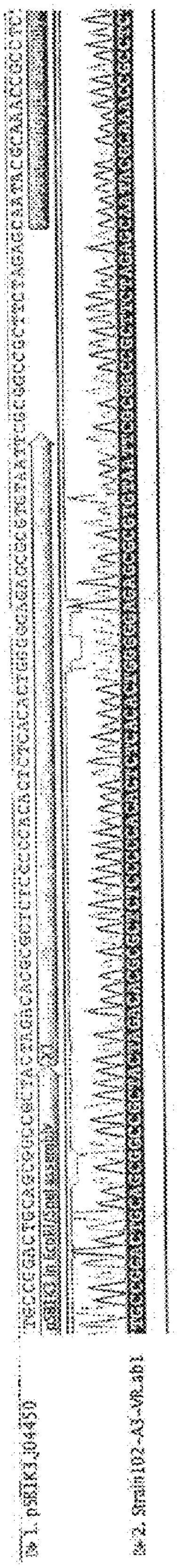
Figure 19B:
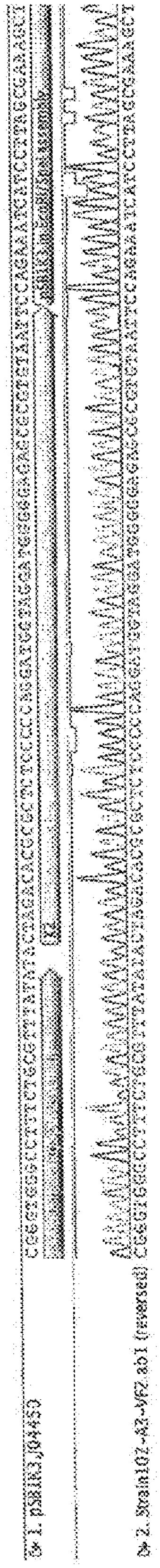

FIG. 19 shows representative sequence analysis at the part junctions for a 2-part assembly constructed using EcoRI/SpeI pSB1K3.J04450. FIG. 19A shows the sequence of the standard part/linker sequence X1between pSB1K3 and J04450 (SEQ ID NO: 47), and FIG. 19B shows the sequence of the standard part/linker sequence X2 between J04450 and pSB1K3 (SEQ ID NO: 48).

Figure 20A:
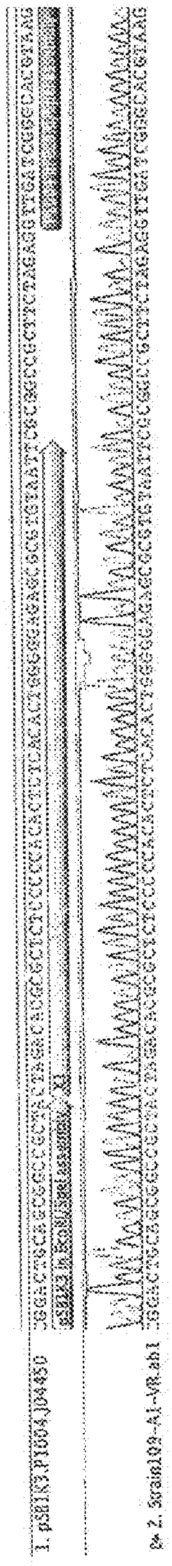
Figure 20B:
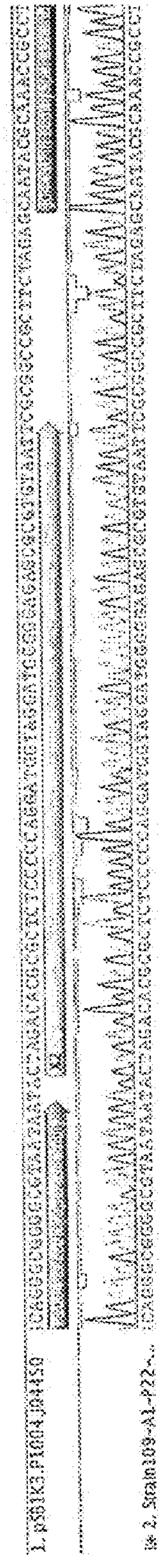

FIG. 20 shows representative sequence analysis at the part junctions for a 3-part assembly constructed using EcoRI/SpeI (pSB1K3.P1004.J04450). FIG. 20A shows the sequence of the standard part/linker sequence Xl between pSB1K3 and P1004 (SEQ ID NO: 49), FIG. 20B shows the sequence of the standard part/linker sequence X2 between P1004 and J04450

Figure 20C:
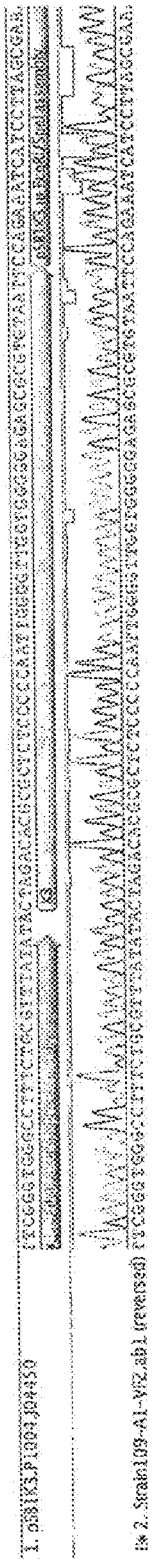

(SEQ ID NO: 50), and FIG. 20C shows the sequence of the standard part/linker sequence X3between J04450 and pSB1K3 (SEQ ID NO: 51).

FIG. 21 shows the predicted sequence of the entire pSB1C3J7101.P1003 three part assembly (construct 5, SEQ ID NO: 52). The numbering used in the annotations at the top of FIG. 21 refers to the numbering of the nucleotides in the sequence itself. Accordingly, nucleotides 1 to 103 consist of the pSB1C3 part, nucleotides 104 to 106 are the SL overhang and so on.

EXAMPLES

Example 1

Red and Blue Colony DNA Assembly Assays

Assay Description

Two assays were developed that use the same experimental protocol but different sets of input parts (nucleic acids) and oligos (linkers) for the DNA assembly reactions. The first assay generates blue colonies as a result of successful DNA assembly due to the expression of lacZa as a reporter protein and the second assay generates red colonies due to the expression of mRFP1.

A correct DNA assembly reaction will insert a ribosome binding site (RBS) between the transcriptional promoter (R0040 or R0010) and the reporter protein (lacZa or mRFP1). Proper insertion of this RBS results in a complete operon for expression of the reporter protein, resulting in a phenotypic change. Incorrect assemblies will leave the colonies colourless. This assay was demonstrated by determining the efficiency of a 1 part assembly using the parts and oligos shown in FIG. 9 and listed in Table 1. Coloured and colourless colonies were sequence verified.

This assay describes a 1 part assembly but can be applied for 2 and 3 part assemblies by assembling the sub-components such as mRFP1, B0034, and R0010 (in the case of the red assay). Each of these parts is independently essential for producing the phenotypic change in the transformed cells.

TABLE 1

Sequence of oligos used in the 1 part assemblies for demonstrating the red and blue colony screening assays. 5phos indicates the presence of a 5' phosphate on the oligo.

| | |
|---|---|
| lacZa Linker Oligo | /5phos/gccaaagaggagaaatactagat (SEQ ID NO: 20) |
| lacZa Part Oligo | /5phos/gtcatctagtatttctcctcttt (SEQ ID NO: 21) |
| mRFP1 Linker Oligo | /5phos/gccaaagaggagaaatactaga (SEQ ID NO: 22) |
| mRFP1 Part Oligo | /5phos/ccatctagtatttctcctcttt (SEQ ID NO: 23) |

Assay Experimental Protocol

Step 1: Digest lacZa.pSB1C3 (Blue) or mRFP1.pSB1C3 (Red) Parts Using the EarI Restriction Endonuclease (NEB Catalog #R05281.)

Digest Mix

4 μL NEB Buffer 4

1 μL Ear I

X μL DNA (add 1 μg of DNA)

35—X μL water (bring to a total 20 μL reaction volume with water)

Digest at 37° C. for 2 hours, followed by heat killing the enzyme at 80° C. for 20 minutes.

Step 2: PCR Purification Using a Qiagen™ QIAquick™ PCR Purification Kit (Qiagen™ Catalog #28106)

Follow instructions included in the Qiagen™ kit. The only equipment needed is a tabletop centrifuge for spinning eppendorf tubes.

Step 3: Ligation Using T4 DNA Ligase (NEB Catalog#M0202M)

Ligation Mix

4 μL Digested lacZa.pSB1C3 or mRFP1.pSB1C3

2 μL Part oligo (50 μM)

2 μL Linker oligo (5004)

2 μL T4 DNA Ligase Buffer 9.54 Water 0.5 μL T4 DNA Ligase

Ligate at 16° C. for 2 hours.

Step 4 (optional step): Digest with BamH1 (Neb Catalog#R0136L)

Add 5 μL NEB Buffer 3 and 1 μL BamH1 directly to the ligation mix and incubate for 2 hours at 37° C. This step digests plasmid backbone that was not cut in the original EarI digest (Step 1) in order to reduce background in the assay.

Step 5: Transformation into One Shot TOP10 Chemically Competent *E. coli* (Invitrogen Catalog #C4040-10)

Add 2 μL of the Mix from Step 4 to thawed competent cells. Follow instructions for heat shock and transformation from Invitrogen. Plate onto LB plates containing Chloramphenicol antibiotic (Red) or Chloramphenicol and IPTG/X-gal (Blue). Grow plates overnight at 37° C.

Step 6: Count colonies that display the correct phenotype (red or blue colouring) relative to the total number of colonies. The coloured colonies represent correct assemblies and the fraction of coloured colonies provides a measure of the DNA assembly efficiency.

Results

The red (RFP-based) colony assay is an improvement over the blue (lacZ-based) colony assay. The lacZ gene contains an EarI site which creates additional digestion and ligation events that are not part of the core DNA Assembly process, while RFP contains no EarI sites. The red colony assay had a much higher efficiency, showing 977/1050 colonies red (93%) while the blue colony assay showed only ~50% correct (blue) colonies. The lower efficiency of the blue colony assay was expected to be due to the presence of the internal EarI site in the lacZ gene. Four of each of the coloured and non-coloured colonies were sequenced. This confirmed that the coloured colonies were correct assemblies and the non-coloured colonies were incorrect. Finally, the assembly reaction was run without adding the assembly oligos (negative control) and it was found that all oligos were colourless as expected.

Example 2

Two, Three and Four Part DNA Assemblies

DNA Assembly Description

Multiple 2-part, 3-part and 4-part assemblies (polynucleic acid sequences) were assembled from a set of nine initial component parts (nucleic acid sequences). The assemblies were verified by visual screening (reporters) as well as antibiotic selection (vector backbones and antibiotic resistance parts). They were further verified by colony PCR reactions using oligos within the assembled parts. The assemblies were then finally confirmed by direct sequencing of the entire construct.

The assembly method was varied in two ways:

(1) Different methods of purification were used following the part-linker assembly step—DNA purification spin columns and gel extraction.

(2) Two different enzymes were used to digest the parts before the part assembly stage—EarI (Type IIS restriction enzyme) or EcoRI-SpeI (pair of traditional restriction enzymes used for BioBrick™ assembly).

Correct assemblies were produced using 3 different approaches: Spin column/EarI digest, Spin column/EcoRI-SpeI digest, and Gel extraction/EcoRI-SpeI digest.

The 3 different assembly approaches all used the same overall DNA assembly scheme that relies on partially double-stranded oligos and is shown in FIG. 6.

DNA Assembly Experimental Protocol

1. Media and Culture Conditions

Bacterial cultures were grown in Magnificent Broth (MacConnell Research, CA) supplemented with antibiotics (Sigma-Aldrich) as appropriate. Cultures were grown at 37° C. with rotation at 200 rpm in deep-well plates for 12-14 hours.

2. DNA Purification

Plasmids were purified from bacterial cultures using mini-prep kits (Qiagen™ Macherey-Nagel). Plasmid concentrations were measured by comparison to DNA standards that were run in parallel on electrophoretic gels.

3. Restriction Digest 1-3 μg of plasmid DNA was digested for 2-4 hours at 37° C. and not heat-inactivated. The restriction digests contained 4 μl of a 10× reaction buffer, 0.4 μl of a 100×BSA solution, and 1 μl of each appropriate restriction enzyme and the reactions were made to a final volume of 40 μl with deionized water. Enzymes and buffers were obtained from New England Biolabs (Beverley, Mass.). BioBrick™ parts were digested with EcoRI-HF and SpeI while EarI parts were digested with EarI alone.

4. Oligonucleotide Preparation

Oligos were ordered from Integrated DNA Technologies or Invitrogen and resuspended in TE at 10 μM for storage. 5' phosphates were added to the oligos by the manufacturer (indicated by /5Phos/). Further dilutions of the oligos were made immediately prior to use in deionized water.

```
std-complement:
                                    (SEQ ID NO: 1)
/5Phos/gggggagagcgcgtgt

X1-P1-EarI:
                                    (SEQ ID NO: 2)
/5Phos/cggacacgcgctctcccccacactctcacact

X1-L1-EarI:
                                    (SEQ ID NO: 3)
/5Phos/gccacacgcgctctcccccagtgtgagagtgt

X2-P1-EarI:
                                    (SEQ ID NO: 4)
/5Phos/cggacacgcgctctcccccaggatggtaggat

X2-L1-EarI:
                                    (SEQ ID NO: 5)
/5Phos/gccacacgcgctctcccccatcctaccatcct
```

-continued

```
X3-P1-EarI:
                                    (SEQ ID NO: 6)
/5Phos/cggacacgcgctctcccccaattggggttggt

X3-L1-EarI:
                                    (SEQ ID NO: 7)
/5Phos/gccacacgcgctctcccccaccaaccccaatt

X4-P1-EarI:
                                    (SEQ ID NO: 8)
/5Phos/cggacacgcgctctcccccgattacaccggag

X4-L1-EarI:
                                    (SEQ ID NO: 9)
/5Phos/gccacacgcgctctcccccctccggtgtaatc

X1-P1-SpeI:
                                    (SEQ ID NO: 10)
/5Phos/ctagacacgcgctctcccccacactctcacact

X1-L1-EcoRI:
                                    (SEQ ID NO: 11)
/5Phos/aattacacgcgctctcccccagtgtgagagtgt

X2-P1-SpeI:
                                    (SEQ ID NO: 12)
/5Phos/ctagacacgcgctctcccccaggatggtaggat

X2-L1-EcoRI:
                                    (SEQ ID NO: 13)
/5Phos/aattacacgcgctctcccccatcctaccatcct

X3-P1-SpeI:
                                    (SEQ ID NO: 14)
/5Phos/ctagacacgcgctctcccccaattggggttggt

X3-L1-EcoRI:
                                    (SEQ ID NO: 15)
/5Phos/aattacacgcgctctcccccaccaaccccaatt

X4-P1-SpeI:
                                    (SEQ ID NO: 16)
/5Phos/ctagacacgcgctctcccccgattacaccggag

X4-L1-EcoRI:
                                    (SEQ ID NO: 17)
/5Phos/aattacacgcgctctcccccctccggtgtaatc
```

The oligos are named based on FIG. 6, e.g. $X^3$-P1-EcoRI is the first part oligo for the third standard linker that is designed to be complementary to the overhang generated by an EcoRI digest. All part-linker oligos were designed to have a common second stranded oligo (std-complement). Thus, std-complement serves serves as both L2 and P2 for all Xn.

For EarI-digested parts, a common 5'-overhang of ggc on the 3'-end and ccg on the 5'-end of each part was used.

5. Part-Linker Ligations

Oligo annealing and ligation to the restriction digest fragments was performed in a single reaction vessel. An appropriate set of linker oligos was chosen for each assembly. The phase 1 and 2 (part preparation and part/linker assembly) steps were combined. For example, for a 3-part assembly using EarI digested parts, we could choose the oligo linker set X1 for the first part, X2 for the second part, and X3 for the third part. The first part would be ligated to the oligos std-complement, X1-P1-EarI, and X2-L1-EarI. The second part would be ligated to the oligos std-complement, X2-P1-EarI, and X3-P1-EarI. The third part would be ligated to the oligos std-complement, X3-P1-EarI, and X1-P1-EarI.

An initial reaction mix of 10 μl of restriction digest, 10 μl of the appropriate part and linker oligos (to a final concentration of ~6 nM), 1 μl of the complementary oligo (std-complement)

(to a final concentration of 24 nM), 3 μl of 10×T4 DNA ligase buffer (New England Biolabs, MA) and 4 μl of water was heated to 65° C. in a thermocycler (Eppendorf) and the temperature ramped down to room temperature over 10 min. This step was intended to melt any pre-existing secondary structure in the oligonucleotides and to allow cognate oligos to anneal. 1 μl of T4 DNA ligase (New England Biolabs, MA) and 1 μl of the same restriction enzymes used in the digests was then added to the reactions. The reactions were incubated at 4° C. for 12 hours. The addition of the restriction enzymes was intended to prevent religation of the digested fragments.

6. Part-Linker Purification

The part-linker pairs were then purified using a QiaQuick™ PCR purification kit (Qiagen™) or via gel electrophoresis and extraction via a QiaQuick™ gel extraction kit (Qiagen™). DNA was eluted in 40 μl of Elution Buffer EB (Qiagen™)

7. Pathway Assembly

The purified part-linker DNA for the two, three, or four parts to be assembled was combined in a pathway assembly reaction. 10 μl of each part-linker pair (or 7.5 μl in the case of a four part assembly) was mixed with 4 μl of 10×T4 DNA ligase buffer (New England Biolabs) and brought to a final volume of 37 μl by the addition of deionized water. The reactions were heated and cooled as described in part-linker ligation section above. Again 1 μl of T4 DNA ligase (New England Biolabs) and 1 μl of each of restriction enzymes used previously was added and the reactions incubated at room temperature for 30 min.

8. Transformation 2 μl of the Pathway assembly reactions were added to thawed chemically competent NEB-10beta cells (New England Biolabs) and incubated on ice for 30 min. The cells were heat-shocked at 42° C. for 45 s and incubated on ice for a further 2 min. 200 μl of SOC medium (New England Biolabs) was added to the cells, which were then incubated at 37° C. for 2 hours with rotation at 200 rpm in a deep-well plate. 200 μl of the cells were then plated on LB agar plates containing the appropriate antibiotics (Teknova, Calif.) and incubated at 37° C. overnight.

9. Selection and Verification of Clones

Colonies from the antibiotic plates were picked into 20 μl of deionized water and 2 μl of the cell suspensions were pipetted onto 4 plates containing each of the four antibiotics being used (Ampicillin, Chloramphenicol, Kanamycin, and Tetracycline). These plates were incubated at 37° C. for 8 hours to confirm the set of antibiotic resistances carried by the clones. 1 μl of the cell suspensions was added to a 10 μl single-colony PCR reaction containing 5 μl of Taq 2× master mix (New England Biolabs), 3 μl of deionized water, and 0.5 μl of primers VF2 and VR having the following sequences:

```
VF2:      tgccacctgacgtctaagaa    (SEQ ID NO: 24)

VR:       attaccgcctttgagtgagc    (SEQ ID NO: 25)
```

The PCR reactions were incubated at 95° C. for 5 min and then underwent 35 cycles of 94° C. for 15 s, 56° C. for 30 s, and 68° C. for 3 min. A final extension step at 68° C. for 10 min was also performed. The PCR reactions were analyzed via gel electrophoresis to identify those colonies producing amplicons of the expected length. DNA from colonies producing the correct length amplicon and carrying only the correct antiobiotic resistances was sequenced by Genewiz (NJ) and the sequences analyzed by a local alignment algorithm.

Input Parts for DNA Assembly Reactions

Nine input parts were developed for conducting two, three and four part DNA assemblies as follows.

These were all derived from BioBricks™ parts. Names refer to the BBa_(BioBrick™ alpha) group of parts found at http://partsregistry.org. For assembly using EcoRI/SpeI, the parts were used as is. For assembly with EarI, the parts were first moved in a standard way into a standard EarI conversion plasmid. The EarI conversion plasmid was constructed by digestion of a plasmid, such as pSB1C3 or pSB1T3 with EcoRI/PstI and ligating in the oligos:

```
                                        (SEQ ID NO: 18)
aattgctcttcgccgtctagaggatccctgcagcccgaagagcatgca

                                        (SEQ ID NO: 19)
tgctcttcgggctgcagggatcctctagacggcgaagagc
```

This conversion plasmid was then cloned and sequenced verified.

For conversion of BioBrick™ parts into EarI-compatible parts, both the conversion plasmid and the BioBrick™ parts were digested with XbaI/PstI. The BioBrick™ part was ligated into the conversion plasmid and correct clones were screened and sequence verified using standard methods. After verification, these parts became suitable as input to the assembly process with an EarI digest leaving standard 3 nucleotide 5'-overhangs (ggc on the 3'-end and ccg on the 5'-end).

The parts are shown in schematic form in FIG. 10.

Vector Parts:
pSB1C3—chlR
pSB1K3—kanR
pSB1T3—tetR

Antibiotic Resistance Parts:
P1002—AmpR
P1003—KanR
P1004—ChlR
P1005—TetR

Reporter Parts:
J04450—RFP
I7101—GFP

Results Demonstrating Successful DNA Assembly Reactions

Various successful two, three and four part DNA Assembly reactions were demonstrated using different combinations of the 9 input parts and verified by phenotype analysis, length verification and/or sequencing. The means of purification were varied (spin column/gel extraction), as were the restriction enzyme used (EarI or EcoRI/SpeI). FIG. 8 shows the difference in part preparation by the different restriction enzymes.

2 part assembly reactions

Spin Column (EarI):
pSB1C3.I7101—correct by sequencing
pSB1C3.P1002—correct by sequencing
pSB1C3.P1003—correct by sequencing Spin Column (EcoRI/SpeI)
pSB1K3.P1004—correct by sequencing
pSB1K3.J04450—correct by sequencing pSB1C3.P1003—correct by sequencing
pSB1C3.P1005—correct by sequencing
pSB1T3.P1003—correct by sequencing
pSB1T3.P1004—correct by sequencing 3 part assembly reactions Spin Column (EarI):
pSB1C3.P1002.J04450—correct by sequencing
pSB1C3.I7101.P1003—correct by sequencing
pSB1C3.P1002.P1003—correct by sequencing Spin Column (EcoRI/SpeI):
pSB1K3.P1004.J04450—correct except for point deletion in oligo
pSB1C3.P1003.J04450—correct by sequencing Gel Extraction (EcoRI/SpeI)
pSB1K3.P1005.J04450—correct; 3 parts present in correct order, but one seq primer had high background on the chromatogram.
pSB1C3.P1003.J04450—correct by sequencing
pSB1C3.P1005.J04450—correct by sequencing
pSB1T3.P1003.J04450—correct by sequencing
pSB1T3.P1004.J04450—correct by sequencing FIG. 11 is a plasmid map of the pSB1C3.I7101.P1003 three part assembly.

To verify the correct assembly of the three nucleic acid fragments, colony PCR was performed using primers that anneal near the junction between fragments 2 and 3. The expected length of the PCR product for correctly assembled clones is approximately 400 bp. To check the length of the resulting PCR products, the reactions were electrophoresed through a 1% agarose gel and the results can be seen in FIG. 12.

4 Part Assembly Reactions

Spin Column (EarI):
pSB1C3.I7101.P1002.J04450—correct by sequencing
pSB1C3.I7101.P1003.J04450—correct by sequencing
pSB1C3.P1002.P1003.J04450—correct by sequencing Analysis of 2-, 3-, and 4-Part Assemblies Produced Using EarI For each construct, transformants were analyzed by i) phenotype (antibiotic resistance & fluorescence), ii) length of insert in destination vector as determined by Colony PCR, and iii) sequence analysis.

Phenotype Analysis

For each construct, 8 or 16 colonies were picked into 20 μl of H$_2$O and 2 μl was spotted onto plates containing a single antibiotic, either Ampicillin, Chloramphenicol, Kanamycin or Tetracycline. Following overnight growth, spots were checked for growth on the antibiotic plates and for fluorescence using blue light transillumination and an orange filter. The results of the phenotype screen are summarized in Table 2 below. A 1 indicates that a colony grew only on the intended antibiotic resistances, and exhibited the expected fluorescent phenotype. A 0 indicates that the spot responded incorrectly to at least one antibiotic, or exhibited incorrect fluorescence.

TABLE 2

| # | Construct | | | | Phenotype (antibiotic & fluorescence) | | | | | | | | | | | | | | | | Correct |
|---|---|---|---|---|---|---|---|---|---|---|---|---|---|---|---|---|---|---|---|---|---|
| | | | | | 4 part assemblies | | | | | | | | | | | | | | | | |
| 1 | pSB1C3 | I7101 | P1002 | J04450 | 1 | 1 | 1 | 1 | 0 | 0 | 1 | 0 | 1 | 0 | 1 | 1 | 1 | 1 | 1 | 1 | 0.75 |
| 2 | pSB1C3 | I7101 | P1003 | J04450 | 1 | 1 | 1 | 1 | 1 | 0 | 1 | 1 | | | | | | | | | 0.88 |
| 3 | pSB1C3 | P1002 | P1003 | J04450 | 1 | 1 | 1 | 1 | 1 | 1 | 1 | 1 | 1 | 1 | 1 | 1 | 1 | 1 | 0 | 1 | 0.94 |
| | | | | | 3 part assemblies | | | | | | | | | | | | | | | | |
| 4 | pSB1C3 | P1002 | J04450 | | 1 | 1 | 1 | 1 | 1 | 0 | 1 | 1 | | | | | | | | | 0.88 |
| 5 | pSB1C3 | I7101 | P1003 | | 1 | 0 | 1 | 1 | 0 | 0 | 0 | 1 | | | | | | | | | 0.50 |
| 6 | pSB1C3 | P1002 | P1003 | | 1 | 1 | 1 | 0 | 1 | 1 | 1 | 1 | | | | | | | | | 0.88 |
| | | | | | 2 part assemblies | | | | | | | | | | | | | | | | |
| 7 | pSB1C3 | I7101 | | | 1 | 0 | 1 | 1 | 1 | 1 | 1 | 1 | | | | | | | | | 0.88 |
| 8 | pSB1C3 | P1002 | | | 1 | 1 | 1 | 1 | 1 | 1 | 1 | 1 | | | | | | | | | 1.00 |
| 9 | pSB1C3 | P1003 | | | 1 | 1 | 1 | 1 | 1 | 1 | 1 | 1 | | | | | | | | | 1.00 |

Length Verification Via Colony PCR

The same cell suspensions were used as templates for single colony PCR reactions in the following manner.

PCR Reaction Mix—

1 μl cell suspension

3 μl H$_2$O

5 μl 2×Taq 2× Master Mix (New England BioLabs, Ipswich, Mass., USA)

0.5 μl forward primer 0.5 μl reverse primer

Forward primer sequence—5'-tgccacctgacgtctaagaa-3'

Reverse primer—5'-attaccgcctttgagtgagc-3'

PCR Reaction Conditions

95° C. for 10 min

94° C. for 30 sec

56° C. for 30 sec

68° C. for 5 min

72° C. for 10 min

Steps 2 to 4 were repeated 35 times.

The PCR reactions were analyzed by gel electrophoresis and amplicon lengths were compared to a DNA marker ladder (2-log ladder, New England BioLabs). The results of the colony PCR reactions are summarized in Table 3 below, where a 1 indicates the major amplicon length was the length expected for the successful assembly and 0 indicates an incorrect major amplicon band.

TABLE 3

| | Construct | | | | Expected amplicon length | PCR | | | | | | | | | | | | | | | | Fraction Correct |
|---|---|---|---|---|---|---|---|---|---|---|---|---|---|---|---|---|---|---|---|---|---|---|
| | | | | | | 4 part assemblies | | | | | | | | | | | | | | | | |
| 1 | pSB1C3 | I7101 | P1002 | J04450 | 3470 | 1 | 1 | 1 | 0 | 0 | 0 | 1 | 0 | 1 | 0 | 1 | 1 | 1 | 1 | 1 | 1 | 0.69 |
| 2 | pSB1C3 | I7101 | P1003 | J04450 | 3494 | 1 | 1 | 1 | 1 | 1 | 0 | 1 | 1 | | | | | | | | | 0.88 |
| 3 | pSB1C3 | P1002 | P1003 | J04450 | 3499 | 1 | 1 | 1 | 1 | 1 | 1 | 1 | 1 | 1 | 1 | 1 | 1 | 1 | 1 | 0 | 1 | 0.94 |
| | | | | | | 3 part assemblies | | | | | | | | | | | | | | | | |
| 4 | pSB1C3 | P1002 | J04450 | | 2481 | 1 | 1 | 1 | 1 | 1 | 0 | 1 | 1 | | | | | | | | | 0.88 |
| 5 | pSB1C3 | I7101 | P1003 | | 2374 | 0 | 1 | 0 | 1 | 1 | 0 | 1 | 0 | | | | | | | | | 0.50 |
| 6 | pSB1C3 | P1002 | P1003 | | 2379 | 1 | 1 | 1 | 1 | 1 | 1 | 1 | 1 | | | | | | | | | 1.00 |
| | | | | | | 2 part assemblies | | | | | | | | | | | | | | | | |
| 7 | pSB1C3 | I7101 | | | 1356 | 1 | 0 | 0 | 1 | 1 | 1 | 1 | 1 | | | | | | | | | 0.75 |
| 8 | pSB1C3 | P1002 | | | 1361 | 1 | 1 | 1 | 1 | 1 | 1 | 1 | 1 | | | | | | | | | 1.00 |
| 9 | pSB1C3 | P1003 | | | 1385 | 1 | 1 | 1 | 1 | 1 | 1 | 1 | 1 | | | | | | | | | 1.00 |

Images of the gels used in this analysis are shown in FIGS. 13, 14 and 15.

Sequence Analysis

For each construct, several clones that passed the phenotypic and length verification screens were sequenced using multiple primers to obtain coverage of the insert part(s) and the plasmid sequence bracketing the insert part(s). For each construct listed above, at least one clone was shown to contain the correct sequence.

Representative sequence analysis at the part junctions is shown in FIG. 16 (construct 9, 2 parts), FIG. 17 (construct 5, 3 parts) and FIG. 18 (construct 2, 4 parts)

The predicted sequence of the entire pSB1C3.I7101.P1003 three part assembly (construct 5) is shown in FIG. 21.

Representative sequence analysis at the part junctions is also shown in FIG. 19 for a 2-part assembly constructed using EcoRI/SpeI (pSB1K3.J04450) and in FIG. 20 for a 3-part assembly constructed using EcoRI/SpeI (pSB1K3.P1004.J04450).

The invention claimed is:

1. A method for the assembly of a polynucleic acid sequence from a plurality of nucleic acid sequences in which the polynucleic acid sequence is of a formula $N_{n+1}$, in which N represents a nucleic acid sequence and where n is 1 or greater than 1 and each N may be the same or a different nucleic acid sequence, in which the method comprises:

(i) providing a first nucleic acid sequence N1 in a vector, using a restriction enzyme to cut the nucleic acid sequence out from the vector and ligating an oligonucleotide linker sequence $L1^{3'}$ to the 3'-end of the nucleic acid sequence;

(ii) providing a second nucleic acid sequence N2 in a vector, using a restriction enzyme to cut the nucleic acid sequence out from the vector, optionally ligating an oligonucleotide linker sequence $L2^{3'}$ to the 3'-end of the nucleic acid sequence and ligating an oligonucleotide linker sequence $L2^{5'}$ to the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1;

(iii) optionally providing one or more additional nucleic acid sequence(s) N in one or more vector(s), using a restriction enzyme to cut the nucleic acid sequence(s) out from the vector(s), wherein nucleic acid sequence N2 has an oligonucleotide linker sequence $L2^{3'}$ at the 3'-end of the nucleic acid sequence, and wherein said one or more additional nucleic acid sequences N comprises a terminal additional nucleic acid sequence NZ, and ligating an oligonucleotide linker sequence to the 3'-end of each additional nucleic acid sequence N, wherein said terminal additional nucleic acid sequence NZ optionally lacks an oligonucleotide linker sequence at its 3'-end, and ligating an oligonucleotide linker sequence to the 5'-end of each additional nucleic acid sequence N, wherein for the first additional nucleic acid sequence N3 the 5'-end linker sequence $L3^{5'}$ is complementary to the 3'-end linker sequence $L2^{3'}$ of nucleic acid sequence N2 and for each second and subsequent additional nucleic acid sequence N the 5'-end linker sequence is complementary to the 3'-end linker sequence of the respective preceding additional nucleic acid sequence; and (iv) ligating said nucleic acid sequences to form said polynucleic acid sequence.

2. A method according to claim 1, wherein said first nucleic acid sequence N1 has an oligonucleotide linker sequence $L1^{5'}$ at the 5'-end of the nucleic acid sequence.

3. A method according to claim 1, wherein said second nucleic acid sequence N2 has an oligonucleotide linker sequence $L2^{3'}$ at the 3'-end of the nucleic acid sequence.

4. A method according to claim 1, wherein said terminal additional nucleic acid sequence NZ has an oligonucleotide linker sequence $LZ^{3'}$ at the 3'-end of the nucleic acid sequence.

5. A method according to claim 3, wherein said first nucleic acid sequence N1 has an oligonucleotide linker sequence $L1^{5'}$ at the 5'-end of the nucleic acid sequence; wherein said second nucleic acid sequence N2 has an oligonucleotide linker sequence $L2^{3'}$ at the 3'-end of the nucleic acid sequence; and wherein the 5'-end linker sequence $L1^{5'}$ of nucleic acid sequence N1 is complementary to the 3'-end linker sequence $L2^{3'}$ of nucleic acid sequence N2.

6. A method according to claim 4, wherein said first nucleic acid sequence N1 has an oligonucleotide linker sequence $L1^{5'}$ at the 5'-end of the nucleic acid sequence; wherein said terminal additional nucleic acid sequence NZ has an oligonucleotide linker sequence $LZ^{3'}$ at the 3'-end of the nucleic acid sequence; and wherein the 5'-end linker sequence $L1^{5'}$ of nucleic acid sequence N1 is complementary to the 3'-end linker sequence $LZ^{3'}$ of nucleic acid sequence NZ.

7. A method according to claim 1, wherein each of said 3'-end linker sequences and said 5'-end linker sequences is partially double stranded.

8. A method according to claim 1, wherein each said nucleic acid sequence has an overhang at each end.

9. A method according to claim 8, wherein said overhang at each end of said nucleic acid sequence is produced by digestion with one or more restriction enzymes.

10. A method according to claim 8, wherein said overhang is 3 or 4 nucleotides in length.

11. A method according to claim 8, wherein the overhang at the 3'-end of the nucleic acid sequence and/or at the 5'-end of the nucleic acid sequence is the same for each nucleic acid sequence.

12. A method according to claim 1, wherein said nucleic acid sequences are purified immediately prior to step (iv).

13. A method according to claim 12, wherein said nucleic acid sequences are purified using a method selected from the group consisting of DNA purification spin columns, gel extraction and biotin-based purification.

14. A method according to claim 1, wherein each said nucleic acid sequence is a protein coding sequence or a regulatory or control element.

15. A method according to claim 1, wherein step (iv) is carried out using DNA ligase.

16. A method for the preparation of a library of polynucleic acid sequences, the method comprising simultaneously producing a plurality of different polynucleic acid sequences using the method of claim 1.

* * * * *

SEQUENCE LISTING

```
<160> NUMBER OF SEQ ID NOS: 52

<210> SEQ ID NO 1
<211> LENGTH: 16
<212> TYPE: DNA
<213> ORGANISM: Artificial
<220> FEATURE:
<223> OTHER INFORMATION: std complement oligonucleotide

<400> SEQUENCE: 1

gggggagagc gcgtgt                                                  16


<210> SEQ ID NO 2
<211> LENGTH: 32
<212> TYPE: DNA
<213> ORGANISM: Artificial
<220> FEATURE:
<223> OTHER INFORMATION: X1-P1-EarI oligonucleotide

<400> SEQUENCE: 2

cggacacgcg ctctccccca cactctcaca ct                                32


<210> SEQ ID NO 3
<211> LENGTH: 32
<212> TYPE: DNA
<213> ORGANISM: Artificial
<220> FEATURE:
<223> OTHER INFORMATION: X1-L1-EarI oligonucleotide

<400> SEQUENCE: 3

gccacacgcg ctctccccca gtgtgagagt gt                                32


<210> SEQ ID NO 4
<211> LENGTH: 32
<212> TYPE: DNA
```

<213> ORGANISM: Artificial
<220> FEATURE:
<223> OTHER INFORMATION: X2-P1-EarI oligonucleotide

<400> SEQUENCE: 4
cggacacgcg ctctccccca ggatggtagg at 32

<210> SEQ ID NO 5
<211> LENGTH: 32
<212> TYPE: DNA
<213> ORGANISM: Artificial
<220> FEATURE:
<223> OTHER INFORMATION: X2-L1-EarI oligonucleotide

<400> SEQUENCE: 5
gccacacgcg ctctccccca tcctaccatc ct 32

<210> SEQ ID NO 6
<211> LENGTH: 32
<212> TYPE: DNA
<213> ORGANISM: Artificial
<220> FEATURE:
<223> OTHER INFORMATION: X3-P1-EarI oligonucleotide

<400> SEQUENCE: 6
cggacacgcg ctctccccca attggggttg gt 32

<210> SEQ ID NO 7
<211> LENGTH: 32
<212> TYPE: DNA
<213> ORGANISM: Artificial
<220> FEATURE:
<223> OTHER INFORMATION: X3-L1-EarI oligonucleotide

<400> SEQUENCE: 7
gccacacgcg ctctccccca ccaaccccaa tt 32

<210> SEQ ID NO 8
<211> LENGTH: 32
<212> TYPE: DNA
<213> ORGANISM: Artificial
<220> FEATURE:
<223> OTHER INFORMATION: X4-P1-EarI oligonucleotide

<400> SEQUENCE: 8
cggacacgcg ctctcccccg attacaccgg ag 32

<210> SEQ ID NO 9
<211> LENGTH: 32
<212> TYPE: DNA
<213> ORGANISM: Artificial
<220> FEATURE:
<223> OTHER INFORMATION: X4-L1-EarI oligonucleotide

<400> SEQUENCE: 9
gccacacgcg ctctcccccc tccggtgtaa tc 32

<210> SEQ ID NO 10
<211> LENGTH: 33
<212> TYPE: DNA
<213> ORGANISM: Artificial
<220> FEATURE:
<223> OTHER INFORMATION: X1-P1-SpeI oligonucleotide

<400> SEQUENCE: 10
ctagacacgc gctctccccc acactctcac act 33

<210> SEQ ID NO 11
<211> LENGTH: 33
<212> TYPE: DNA
<213> ORGANISM: Artificial
<220> FEATURE:
<223> OTHER INFORMATION: X1-L1-EcoRI oligonucleotide

<400> SEQUENCE: 11
aattacacgc gctctccccc agtgtgagag tgt 33

<210> SEQ ID NO 12
<211> LENGTH: 33
<212> TYPE: DNA
<213> ORGANISM: Artificial
<220> FEATURE:
<223> OTHER INFORMATION: X2-P1-SpeI oligonucleotide

<400> SEQUENCE: 12
ctagacacgc gctctccccc aggatggtag gat 33

<210> SEQ ID NO 13
<211> LENGTH: 33
<212> TYPE: DNA
<213> ORGANISM: Artificial
<220> FEATURE:
<223> OTHER INFORMATION: X2-L1-EcoRI oligonucleotide

<400> SEQUENCE: 13
aattacacgc gctctccccc atcctaccat cct 33

<210> SEQ ID NO 14
<211> LENGTH: 33
<212> TYPE: DNA
<213> ORGANISM: Artificial
<220> FEATURE:
<223> OTHER INFORMATION: X3-P1-SpeI oligonuleotide

<400> SEQUENCE: 14
ctagacacgc gctctccccc aattggggtt ggt 33

<210> SEQ ID NO 15
<211> LENGTH: 33
<212> TYPE: DNA
<213> ORGANISM: Artificial
<220> FEATURE:
<223> OTHER INFORMATION: X3-L1-EcoRI oligonucleotide

<400> SEQUENCE: 15
aattacacgc gctctccccc accaacccca att 33

<210> SEQ ID NO 16
<211> LENGTH: 33
<212> TYPE: DNA
<213> ORGANISM: Artificial
<220> FEATURE:
<223> OTHER INFORMATION: X4-P1-SpeI oligonucleotide

<400> SEQUENCE: 16
ctagacacgc gctctccccc gattacaccg gag 33

<210> SEQ ID NO 17
<211> LENGTH: 33
<212> TYPE: DNA
<213> ORGANISM: Artificial
<220> FEATURE:

<223> OTHER INFORMATION: X4-L1-EcoRI oligonucleotide

<400> SEQUENCE: 17
aattacacgc gctctccccc ctccggtgta atc                                33

<210> SEQ ID NO 18
<211> LENGTH: 48
<212> TYPE: DNA
<213> ORGANISM: Artificial
<220> FEATURE:
<223> OTHER INFORMATION: oligo

<400> SEQUENCE: 18
aattgctctt cgccgtctag aggatccctg cagcccgaag agcatgca                 48

<210> SEQ ID NO 19
<211> LENGTH: 40
<212> TYPE: DNA
<213> ORGANISM: Artificial
<220> FEATURE:
<223> OTHER INFORMATION: oligo

<400> SEQUENCE: 19
tgctcttcgg gctgcaggga tcctctagac ggcgaagagc                          40

<210> SEQ ID NO 20
<211> LENGTH: 23
<212> TYPE: DNA
<213> ORGANISM: Artificial
<220> FEATURE:
<223> OTHER INFORMATION: lacZa Linker Oligo

<400> SEQUENCE: 20
gccaaagagg agaaatacta gat                                            23

<210> SEQ ID NO 21
<211> LENGTH: 23
<212> TYPE: DNA
<213> ORGANISM: Artificial
<220> FEATURE:
<223> OTHER INFORMATION: lacZa Part oligo

<400> SEQUENCE: 21
gtcatctagt atttctcctc ttt                                            23

<210> SEQ ID NO 22
<211> LENGTH: 22
<212> TYPE: DNA
<213> ORGANISM: Artificial
<220> FEATURE:
<223> OTHER INFORMATION: mRFP1 Linker Oligo

<400> SEQUENCE: 22
gccaaagagg agaaatacta ga                                             22

<210> SEQ ID NO 23
<211> LENGTH: 22
<212> TYPE: DNA
<213> ORGANISM: Artificial
<220> FEATURE:
<223> OTHER INFORMATION: mRFP1 Part Oligo

<400> SEQUENCE: 23
ccatctagta tttctcctct tt                                             22

-continued

```
<210> SEQ ID NO 24
<211> LENGTH: 20
<212> TYPE: DNA
<213> ORGANISM: Artificial
<220> FEATURE:
<223> OTHER INFORMATION: VF2 primer

<400> SEQUENCE: 24

tgccacctga cgtctaagaa                                              20


<210> SEQ ID NO 25
<211> LENGTH: 20
<212> TYPE: DNA
<213> ORGANISM: Artificial
<220> FEATURE:
<223> OTHER INFORMATION: VR primer

<400> SEQUENCE: 25

attaccgcct ttgagtgagc                                              20


<210> SEQ ID NO 26
<211> LENGTH: 20
<212> TYPE: DNA
<213> ORGANISM: Artificial
<220> FEATURE:
<223> OTHER INFORMATION: Forward primer

<400> SEQUENCE: 26

tgccacctga cgtctaagaa                                              20


<210> SEQ ID NO 27
<211> LENGTH: 20
<212> TYPE: DNA
<213> ORGANISM: Artificial
<220> FEATURE:
<223> OTHER INFORMATION: Reverse primer

<400> SEQUENCE: 27

attaccgcct ttgagtgagc                                              20


<210> SEQ ID NO 28
<211> LENGTH: 6
<212> TYPE: DNA
<213> ORGANISM: Artificial
<220> FEATURE:
<223> OTHER INFORMATION: EcoRI restriction site

<400> SEQUENCE: 28

gaattc                                                              6


<210> SEQ ID NO 29
<211> LENGTH: 6
<212> TYPE: DNA
<213> ORGANISM: Artificial
<220> FEATURE:
<223> OTHER INFORMATION: SpeI restriction site

<400> SEQUENCE: 29

actagt                                                              6


<210> SEQ ID NO 30
<211> LENGTH: 5
<212> TYPE: DNA
<213> ORGANISM: Artificial
<220> FEATURE:
<223> OTHER INFORMATION: overhang
```

<400> SEQUENCE: 30 aattc 5

<210> SEQ ID NO 31
<211> LENGTH: 6
<212> TYPE: DNA
<213> ORGANISM: Artificial
<220> FEATURE:
<223> OTHER INFORMATION: EcoRI restriction site

<400> SEQUENCE: 31 cttaag 6

<210> SEQ ID NO 32
<211> LENGTH: 6
<212> TYPE: DNA
<213> ORGANISM: Artificial
<220> FEATURE:
<223> OTHER INFORMATION: SpeI restriction site

<400> SEQUENCE: 32 tgatca 6

<210> SEQ ID NO 33
<211> LENGTH: 5
<212> TYPE: DNA
<213> ORGANISM: Artificial
<220> FEATURE:
<223> OTHER INFORMATION: overhang

<400> SEQUENCE: 33 tgatc 5

<210> SEQ ID NO 34
<211> LENGTH: 11
<212> TYPE: DNA
<213> ORGANISM: Artificial
<220> FEATURE:
<223> OTHER INFORMATION: SapI/EarI restriction site 1

<400> SEQUENCE: 34
gctcttcgcc g 11

<210> SEQ ID NO 35
<211> LENGTH: 11
<212> TYPE: DNA
<213> ORGANISM: Artificial
<220> FEATURE:
<223> OTHER INFORMATION: SapI/EarI restriction site 2

<400> SEQUENCE: 35
gcccgaagag c 11

<210> SEQ ID NO 36
<211> LENGTH: 11
<212> TYPE: DNA
<213> ORGANISM: Artificial
<220> FEATURE:
<223> OTHER INFORMATION: SapI/EarI restriction site 3

<400> SEQUENCE: 36
cgagaagcgg c 11

<210> SEQ ID NO 37
<211> LENGTH: 11

<212> TYPE: DNA
<213> ORGANISM: Artificial
<220> FEATURE:
<223> OTHER INFORMATION: SapI/EarI restriction site 4

<400> SEQUENCE: 37
cgggcttctc g 11

<210> SEQ ID NO 38
<211> LENGTH: 90
<212> TYPE: DNA
<213> ORGANISM: Artificial
<220> FEATURE:
<223> OTHER INFORMATION: sequence of the standard part/linker sequence X1 between pSB1C3 and P1003

<400> SEQUENCE: 38
ggaattcgcg gccgcttcta gagccacacg cgctctcccc cagtgtgaga gtgtggggga 60
gagcgcgtgt ccgtctagag ctgatccttc 90

<210> SEQ ID NO 39
<211> LENGTH: 90
<212> TYPE: DNA
<213> ORGANISM: Artificial
<220> FEATURE:
<223> OTHER INFORMATION: sequence of the standard part/linker sequence X2 between P1003 and pSB1C3

<400> SEQUENCE: 39
aatactagta gcggccgctg cagccacacg cgctctcccc catcctacca tcctggggga 60
gagcgcgtgt ccgctgcagt ccggcaaaaa 90

<210> SEQ ID NO 40
<211> LENGTH: 86
<212> TYPE: DNA
<213> ORGANISM: Artificial
<220> FEATURE:
<223> OTHER INFORMATION: sequence of the standard part/linker sequence X1 between pSB1C3 and I7101

<400> SEQUENCE: 40
attcgcggcc gcttctagag ccacacgcgc tctcccccag tgtgagagtg tgggggagag 60
cgcgtgtccg tctagagtcc ctatca 86

<210> SEQ ID NO 41
<211> LENGTH: 86
<212> TYPE: DNA
<213> ORGANISM: Artificial
<220> FEATURE:
<223> OTHER INFORMATION: sequence of the standard part/linker sequence X2 between I7101 and P1003

<400> SEQUENCE: 41
actagtagcg gccgctgcag ccacacgcgc tctcccccat cctaccatcc tgggggagag 60
cgcgtgtccg tctagagctg atcctt 86

<210> SEQ ID NO 42
<211> LENGTH: 86
<212> TYPE: DNA
<213> ORGANISM: Artificial
<220> FEATURE:
<223> OTHER INFORMATION: sequence of the standard part/linker sequence X3 between P1003 and pSB1C3

<400> SEQUENCE: 42
tagtagcggc cgctgcagcc acacgcgctc tcccccacca accccaattg ggggagagcg 60
cgtgtccgct gcagtccggc aaaaaa 86

<210> SEQ ID NO 43
<211> LENGTH: 87
<212> TYPE: DNA
<213> ORGANISM: Artificial
<220> FEATURE:
<223> OTHER INFORMATION: shows the sequence of the standard part/linker sequence X1 between pSB1C3 and I7101

<400> SEQUENCE: 43
gaattcgcgg ccgcttctag agccacacgc gctctccccc agtgtgagag tgtgggggag 60
agcgcgtgtc cgtctagagt ccctatc 87

<210> SEQ ID NO 44
<211> LENGTH: 86
<212> TYPE: DNA
<213> ORGANISM: Artificial
<220> FEATURE:
<223> OTHER INFORMATION: sequence of the standard part/linker sequence X2 between I7101 and P1003

<400> SEQUENCE: 44
tactagtagc ggccgctgca gccacacgcg ctctccccca tcctaccatc ctgggggaga 60
gcgcgtgtcc gtctagagct gatcct 86

<210> SEQ ID NO 45
<211> LENGTH: 86
<212> TYPE: DNA
<213> ORGANISM: Artificial
<220> FEATURE:
<223> OTHER INFORMATION: sequence of the standard part/linker sequence X3 between P1003 and J04450

<400> SEQUENCE: 45
tagtagcggc cgctgcagcc acacgcgctc tcccccacca accccaattg ggggagagcg 60
cgtgtccgtc tagagcaata cgcaaa 86

<210> SEQ ID NO 46
<211> LENGTH: 86
<212> TYPE: DNA
<213> ORGANISM: Artificial
<220> FEATURE:
<223> OTHER INFORMATION: sequence of the standard part/linker sequence X4 between J04450 and pSB1C3

<400> SEQUENCE: 46
ctagtagcgg ccgctgcagc cacacgcgct ctccccccctc cggtgtaatc gggggagagc 60
gcgtgtccgc tgcagtccgg caaaaa 86

<210> SEQ ID NO 47
<211> LENGTH: 110
<212> TYPE: DNA
<213> ORGANISM: Artificial
<220> FEATURE:
<223> OTHER INFORMATION: sequence of the standard part/linker sequence X1 between pSB1K3 and J04450

<400> SEQUENCE: 47
tgccggactg cagcggccgc tactagacac gcgctctccc ccacactctc acactggggg 60
agagcgcgtg taattcgcgg ccgcttctag agcaatacgc aaaccgcctc 110

<210> SEQ ID NO 48
<211> LENGTH: 104
<212> TYPE: DNA
<213> ORGANISM: Artificial
<220> FEATURE:
<223> OTHER INFORMATION: sequence of the standard part/linker sequence
X2 between J04450 and pSB1K3

<400> SEQUENCE: 48
cgggtgggcc tttctgcgtt tatatactag acacgcgctc tcccccagga tggtaggatg 60
ggggagagcg cgtgtaattc cagaaatcat ccttagcgaa agct 104

<210> SEQ ID NO 49
<211> LENGTH: 107
<212> TYPE: DNA
<213> ORGANISM: Artificial
<220> FEATURE:
<223> OTHER INFORMATION: sequence of the standard part/linker sequence
X1 between pSB1K3 and P1004

<400> SEQUENCE: 49
cggcatgcag cggccgctac tagacacgcg ctctccccca cactctcaca ctgggggaga 60
gcgcgtgtaa ttcgcggccg cttctagagg ttgatcgggc acgtaag 107

<210> SEQ ID NO 50
<211> LENGTH: 108
<212> TYPE: DNA
<213> ORGANISM: Artificial
<220> FEATURE:
<223> OTHER INFORMATION: sequence of the standard part/linker sequence
X2 between P1004 and J04450

<400> SEQUENCE: 50
gcagggcggg gcgtaataat actagacacg cgctctcccc caggatggta ggatggggga 60
gagcgcgtgt aattcgcggc cgcttctaga gcaatacgca aaccgcct 108

<210> SEQ ID NO 51
<211> LENGTH: 102
<212> TYPE: DNA
<213> ORGANISM: Artificial
<220> FEATURE:
<223> OTHER INFORMATION: sequence of the standard part/linker sequence
X3 between J04450 and pSB1K3

<400> SEQUENCE: 51
ttcgggtggg cctttctgcg tttatatact agacacgcgc tctcccccaa ttggggttgg 60
tgggggagag cgcgtgtaat tccagaaatc atccttagcg aa 102

<210> SEQ ID NO 52
<211> LENGTH: 4168
<212> TYPE: DNA
<213> ORGANISM: Artificial
<220> FEATURE:
<223> OTHER INFORMATION: sequence of the entire pSB1C3.I7101.P1003 three
part assembly (construct 5)
<220> FEATURE:
<221> NAME/KEY: misc_feature
<222> LOCATION: (1)..(103)
<223> OTHER INFORMATION: /note="pSB1C3"
<220> FEATURE:
<221> NAME/KEY: misc_feature
<222> LOCATION: (104)..(106)
<223> OTHER INFORMATION: /note="S_L overhang"
<220> FEATURE:
<221> NAME/KEY: primer_bind
<222> LOCATION: (107)..(151)
<223> OTHER INFORMATION: /note="Part/Linker Oligos"
<220> FEATURE:
<221> NAME/KEY: misc_feature
<222> LOCATION: (152)..(154)
<223> OTHER INFORMATION: /note="S_P overhang"
<220> FEATURE:
<221> NAME/KEY: misc_feature
<222> LOCATION: (155)..(1119)
<223> OTHER INFORMATION: /note="I7101 (GFP)"
<220> FEATURE:
<221> NAME/KEY: misc_feature
<222> LOCATION: (1120)..(1122)
<223> OTHER INFORMATION: /note="S_L overhang"
<220> FEATURE:
<221> NAME/KEY: primer_bind
<222> LOCATION: (1123)..(1167)
<223> OTHER INFORMATION: /note="Part/Linker Oligos"
<220> FEATURE:
<221> NAME/KEY: misc_feature
<222> LOCATION: (1168)..(1170)
<223> OTHER INFORMATION: /note="S_P overhang"
<220> FEATURE:
<221> NAME/KEY: misc_feature
<222> LOCATION: (1171)..(2164)
<223> OTHER INFORMATION: /note="P1003 (kanR)"
<220> FEATURE:
<221> NAME/KEY: misc_feature
<222> LOCATION: (2165)..(2167)
<223> OTHER INFORMATION: /note="S_L overhang"
<220> FEATURE:
<221> NAME/KEY: primer_bind
<222> LOCATION: (2168)..(2212)
<223> OTHER INFORMATION: /note="Part/Linker Oligos"
<220> FEATURE:
<221> NAME/KEY: misc_feature
<222> LOCATION: (2213)..(2215)
<223> OTHER INFORMATION: /note="S_P overhang"
<220> FEATURE:
<221> NAME/KEY: misc_feature
<222> LOCATION: (2216)..(4168)
<223> OTHER INFORMATION: /note="pSB1C3"

<400> SEQUENCE: 52
cattaaccta taaaaatagg cgtatcacga ggcagaattt cagataaaaa aaatccttag 60
ctttcgctaa ggatgatttc tggaattcgc ggccgcttct agagccacac gcgctctccc 120
ccagtgtgag agtgtggggg agagcgcgtg tccgtctaga gtccctatca gtgatagaga 180
ttgacatccc tatcagtgat agagatactg agcactacta gagtcacaca ggaaagtact 240
agatgcgtaa aggagaagaa cttttcactg gagttgtccc aattcttgtt gaattagatg 300
gtgatgttaa tgggcacaaa ttttctgtca gtggagaggg tgaaggtgat gcaacatacg 360
gaaaacttac ccttaaattt atttgcacta ctggaaaact acctgttcca tggccaacac 420
ttgtcactac tttcggttat ggtgttcaat gctttgcgag atacccagat catatgaaac 480
agcatgactt tttcaagagt gccatgcccg aaggttatgt acaggaaaga actatatttt 540
tcaaagatga cgggaactac aagacacgtg ctgaagtcaa gtttgaaggt gatacccttg 600
ttaatagaat cgagttaaaa ggtattgatt ttaaagaaga tggaaacatt cttggacaca 660
aattggaata caactataac tcacacaatg tatacatcat ggcagacaaa caaaagaatg 720
gaatcaaagt taacttcaaa attagacaca acattgaaga tggaagcgtt caactagcag 780
accattatca acaaaatact ccaattggcg atggccctgt ccttttacca gacaaccatt 840
acctgtccac acaatctgcc ctttcgaaag atcccaacga aaagagagac cacatggtcc 900
ttcttgagtt tgtaacagct gctgggatta cacatggcat ggatgaacta tacaaataat 960
aatactagag ccaggcatca aataaaacga aaggctcagt cgaaagactg ggcctttcgt 1020

-continued

```
tttatctgtt gtttgtcggt gaacgctctc tactagagtc acactggctc accttcgggt   1080
gggcctttct gcgtttatat actagtagcg gccgctgcag ccacacgcgc tctcccccat   1140
cctaccatcc tgggggagag cgcgtgtccg tctagagctg atccttcaac tcagcaaaag   1200
ttcgatttat tcaacaaagc cacgttgtgt ctcaaaatct ctgatgttac attgcacaag   1260
ataaaaatat atcatcatga acaataaaac tgtctgctta cataaacagt aatacaaggg   1320
gtgttatgag ccatattcaa cgggaaacgt cttgctcccg tccgcgctta aactccaaca   1380
tggacgctga tttatatggg tataaatggg ctcgcgataa tgtcgggcaa tcaggtgcga   1440
caatctatcg cttgtatggg aagcccgatg cgccagagtt gtttctgaaa catggcaaag   1500
gtagcgttgc caatgatgtt acagatgaga tggtccgtct caactggctg acggagttta   1560
tgcctctccc gaccatcaag cattttatcc gtactcctga tgatgcgtgg ttactcacca   1620
ccgcgattcc tgggaaaaca gccttccagg tattagaaga atatcctgat tcaggtgaaa   1680
atattgttga tgcgctggcc gtgttcctgc gccggttaca ttcgattcct gtttgtaatt   1740
gtccttttaa cagcgatcgt gtatttcgtc ttgctcaggc gcaatcacgc atgaataacg   1800
gtttggttga tgcgagtgat tttgatgacg agcgtaatgg ctggcctgtt gaacaagtct   1860
ggaaagaaat gcacaagctc ttgccattct caccggattc agtcgtcact catggtgatt   1920
tctcacttga taaccttatt tttgacgagg ggaaattaat aggttgtatt gatgttggac   1980
gggtcggaat cgcagaccgt taccaggacc ttgccattct ttggaactgc ctcggtgagt   2040
tttctccttc attacagaaa cggctttttc aaaaatatgg tattgataat cctgatatga   2100
ataaattgca gtttcatttg atgctcgatg agtttttcta ataatactag tagcggccgc   2160
tgcagccaca cgcgctctcc cccaccaacc ccaattgggg gagagcgcgt gtccgctgca   2220
gtccggcaaa aaaacgggca aggtgtcacc accctgccct ttttctttaa aaccgaaaag   2280
attacttcgc gttatgcagg cttcctcgct cactgactcg ctgcgctcgg tcgttcggct   2340
gcggcgagcg gtatcagctc actcaaaggc ggtaatacgg ttatccacag aatcagggga   2400
taacgcagga aagaacatgt gagcaaaagg ccagcaaaag gccaggaacc gtaaaaaggc   2460
cgcgttgctg gcgtttttcc ataggctccg cccccctgac gagcatcaca aaaatcgacg   2520
ctcaagtcag aggtggcgaa acccgacagg actataaaga taccaggcgt ttccccctgg   2580
aagctccctc gtgcgctctc ctgttccgac cctgccgctt accggatacc tgtccgcctt   2640
tctcccttcg ggaagcgtgg cgctttctca tagctcacgc tgtaggtatc tcagttcggt   2700
gtaggtcgtt cgctccaagc tgggctgtgt gcacgaaccc cccgttcagc ccgaccgctg   2760
cgccttatcc ggtaactatc gtcttgagtc caacccggta agacacgact tatcgccact   2820
ggcagcagcc actggtaaca ggattagcag agcgaggtat gtaggcggtg ctacagagtt   2880
cttgaagtgg tggcctaact acggctacac tagaaggaca gtatttggta tctgcgctct   2940
gctgaagcca gttaccttcg gaaaaagagt tggtagctct tgatccggca aacaaaccac   3000
cgctggtagc ggtggttttt ttgtttgcaa gcagcagatt acgcgcagaa aaaaaggatc   3060
tcaagaagat cctttgatct tttctacggg gtctgacgct cagtggaacg aaaactcacg   3120
ttaagggatt ttggtcatga gattatcaaa aaggatcttc acctagatcc ttttaaatta   3180
aaaatgaagt tttaaatcaa tctaaagtat atatgagtaa acttggtctg acagctcgag   3240
gcttggattc tcaccaataa aaaacgcccg gcggcaaccg agcgttctga acaaatccag   3300
atggagttct gaggtcatta ctggatctat caacaggagt ccaagcgagc tcgatatcaa   3360
attacgcccc gccctgccac tcatcgcagt actgttgtaa ttcattaagc attctgccga   3420
```

-continued

```
catggaagcc atcacaaacg gcatgatgaa cctgaatcgc cagcggcatc agcaccttgt   3480
cgccttgcgt ataatatttg cccatggtga aaacgggggc gaagaagttg tccatattgg   3540
ccacgtttaa atcaaaactg gtgaaactca cccagggatt ggctgagacg aaaaacatat   3600
tctcaataaa ccctttaggg aaataggcca ggttttcacc gtaacacgcc acatcttgcg   3660
aatatatgtg tagaaactgc cggaaatcgt cgtggtattc actccagagc gatgaaaacg   3720
tttcagtttg ctcatggaaa acggtgtaac aagggtgaac actatcccat atcaccagct   3780
caccgtcttt cattgccata cgaaattccg gatgagcatt catcaggcgg gcaagaatgt   3840
gaataaaggc cggataaaac ttgtgcttat ttttctttac ggtctttaaa aaggccgtaa   3900
tatccagctg aacggtctgg ttataggtac attgagcaac tgactgaaat gcctcaaaat   3960
gttctttacg atgccattgg gatatatcaa cggtggtata tccagtgatt tttttctcca   4020
ttttagcttc cttagctcct gaaaatctcg ataactcaaa aaatacgccc ggtagtgatc   4080
ttatttcatt atggtgaaag ttggaacctc ttacgtgccc gatcaactcg agtgccactt   4140
gacgtctaag aaaccattat tatcatga                                      4168
```